(12) United States Patent
Miyake et al.

(10) Patent No.: US 9,972,787 B2
(45) Date of Patent: *May 15, 2018

(54) MATERIAL FOR ORGANIC ELECTROLUMINESCENT DEVICE AND ORGANIC ELECTROLUMINESCENT DEVICE USING THE SAME

(71) Applicant: SAMSUNG DISPLAY CO., LTD., Yongin-si, Gyeonggi-Do (KR)

(72) Inventors: Hideo Miyake, Yokohama (JP); Ichinori Takada, Yokohama (JP)

(73) Assignee: SAMSUNG DISPLAY CO., LTD., Yongin-Si, Gyeonggi-Do (KR)

( * ) Notice: Subject to any disclaimer, the term of this patent is extended or adjusted under 35 U.S.C. 154(b) by 13 days.

This patent is subject to a terminal disclaimer.

(21) Appl. No.: 14/832,292

(22) Filed: Aug. 21, 2015

(65) Prior Publication Data

US 2016/0093810 A1    Mar. 31, 2016

(30) Foreign Application Priority Data

Sep. 25, 2014  (JP) .................................. 2014-195147

(51) Int. Cl.
| | |
|---|---|
| *H01L 51/00* | (2006.01) |
| *H01L 51/50* | (2006.01) |
| *C07D 405/14* | (2006.01) |
| *C07D 407/14* | (2006.01) |
| *C07D 409/14* | (2006.01) |
| *C07D 307/91* | (2006.01) |

(52) U.S. Cl.
CPC ........ *H01L 51/0061* (2013.01); *C07D 307/91* (2013.01); *C07D 405/14* (2013.01); *C07D 407/14* (2013.01); *C07D 409/14* (2013.01); *H01L 51/006* (2013.01); *H01L 51/0052* (2013.01); *H01L 51/0073* (2013.01); *H01L 51/0081* (2013.01); *H01L 51/5056* (2013.01)

(58) Field of Classification Search
None
See application file for complete search history.

(56) References Cited

U.S. PATENT DOCUMENTS

| | | |
|---|---|---|
| 8,580,980 B2 | 11/2013 | Osaka et al. |
| 2013/0264558 A1 | 10/2013 | Matsuki et al. |

FOREIGN PATENT DOCUMENTS

| | | | | |
|---|---|---|---|---|
| EP | 2 532 655 A1 | 12/2012 | | |
| JP | H03-078756 | * 4/1991 | ............... | G03G 5/06 |
| JP | 2008-021687 A | 1/2008 | | |
| KR | 10-1251451 B1 | 4/2013 | | |
| WO | WO 2010/114017 A1 | 10/2010 | | |
| WO | WO 2011/059099 A1 | 5/2011 | | |
| WO | WO 2011/090149 A1 | 7/2011 | | |
| WO | WO 2012/039534 A1 | 3/2012 | | |
| WO | WO 2012/091471 A2 | 7/2012 | | |
| WO | WO 2013/032304 A2 | 3/2013 | | |
| WO | WO 2013/039184 | * 3/2013 | ........... | C07D 307/91 |
| WO | WO 2014/034795 A1 | 3/2014 | | |
| WO | WO 2014/051244 A1 | 4/2014 | | |
| WO | WO 2014/088047 | * 6/2014 | ............... | C07F 7/10 |
| WO | WO 2016/072690 | * 5/2016 | ............... | C09K 11/06 |

* cited by examiner

*Primary Examiner* — Alicia L Otton
(74) *Attorney, Agent, or Firm* — Lee & Morse, P.C.

(57) ABSTRACT

A material for an organic electroluminescent device and an organic electroluminescent device including the same, the material including a monoamine compound represented by the following Formula 1:

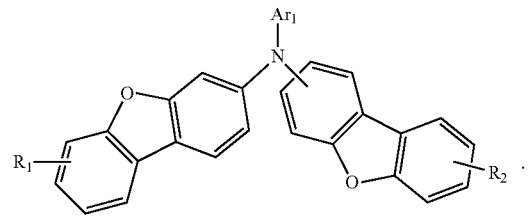

[Formula 1]

6 Claims, 2 Drawing Sheets

MATERIAL FOR ORGANIC ELECTROLUMINESCENT DEVICE AND ORGANIC ELECTROLUMINESCENT DEVICE USING THE SAME

CROSS-REFERENCE TO RELATED APPLICATION

Japanese Patent Application No. 2014-195147, filed on Sep. 25, 2014, in the Japanese Patent Office, and entitled: "Material for Organic Electroluminescent Device and Organic Electroluminescent Device Using the Same," is incorporated by reference herein in its entirety.

BACKGROUND

1. Field

Embodiments relate to a material for an organic electroluminescent device and an organic electroluminescent device using the same.

2. Description of the Related Art

Recently, the development of an organic electroluminescent display is being actively conducted. In addition, the development of an organic electroluminescent device, which is a self-luminescent device used in the organic electroluminescent display, is also being actively conducted.

As the organic electroluminescent device, a structure may include, e.g., an anode, a hole transport layer disposed on the anode, an emission layer disposed on the hole transport layer, an electron transport layer disposed on the emission layer and a cathode disposed on the electron transport layer.

SUMMARY

Embodiments are directed to a material for an organic electroluminescent device and an organic electroluminescent device using the same.

The embodiments may be realized by providing a material for an organic electroluminescent device, the material including a monoamine compound represented by the following Formula 1:

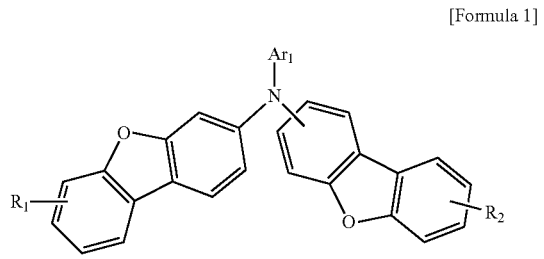

[Formula 1]

wherein, in Formula 1, $R_1$ and $R_2$ are each independently a hydrogen atom, a halogen atom, an alkyl group having 1 to 15 carbon atoms, a substituted or unsubstituted aryl group having 6 to 30 ring carbon atoms, or a substituted or unsubstituted heteroaryl group having 1 to 30 ring carbon atoms, and $Ar_1$ is a moiety represented by the following Formula 2,

—$(Ar_2)_l$—$(Ar_3)_m$—$Ar_4$   [Formula 2]

wherein, in Formula 2, $Ar_2$, $Ar_3$, and $Ar_4$ are each independently a substituted or unsubstituted aryl group having 6 to 50 ring carbon atoms, and l+m is an integer from 0 to 2.

$Ar_1$ may include three combined or condensed substituted or unsubstituted phenyl groups.

$Ar_1$ may include a substituted or unsubstituted phenanthrenyl group.

$Ar_1$ may include a substituted or unsubstituted p-terphenyl group.

$Ar_1$ may include a substituted or unsubstituted naphthalenylphenyl group.

All dibenzofuranyl groups that are directly bonded with a nitrogen atom of the monoamine may be bound to the nitrogen atom at a 3 position of the dibenzofuranyl group.

The compound represented by Formula 1 may include one of the following compounds:

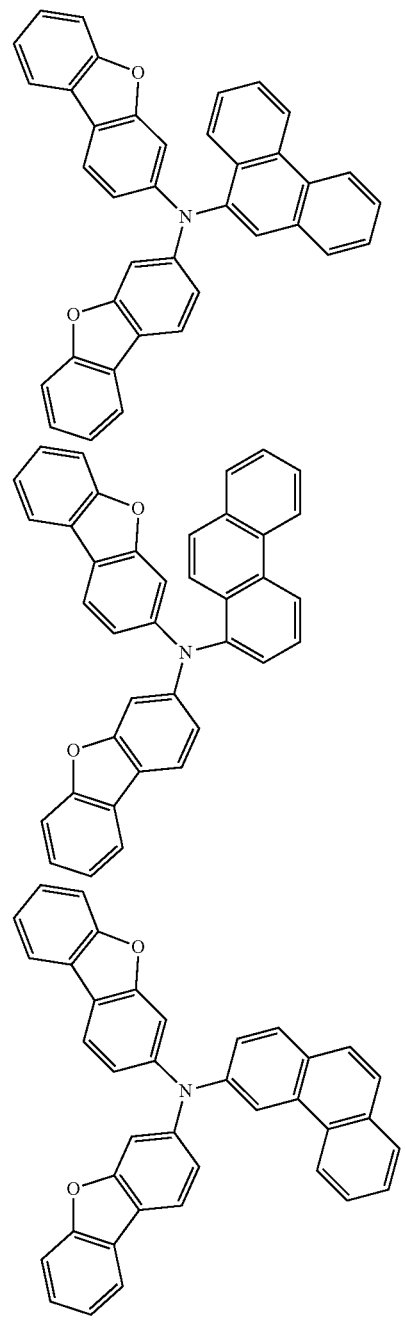

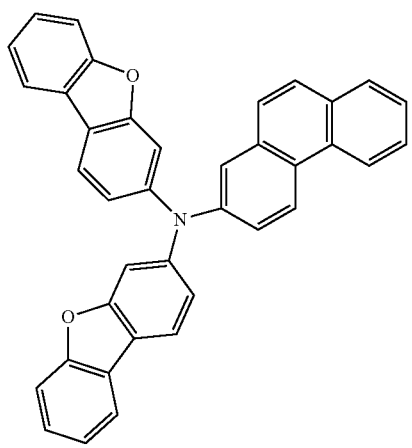
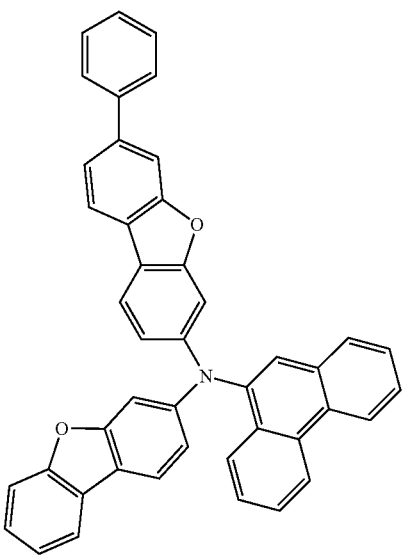
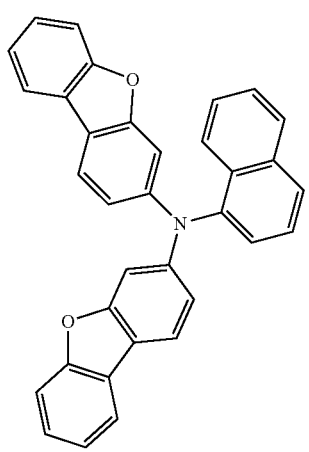
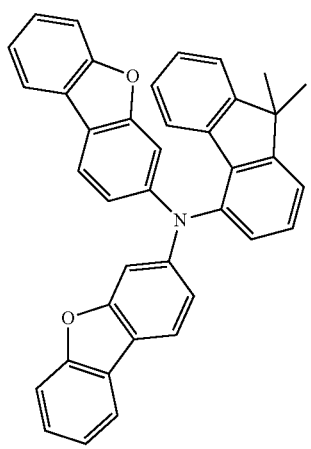
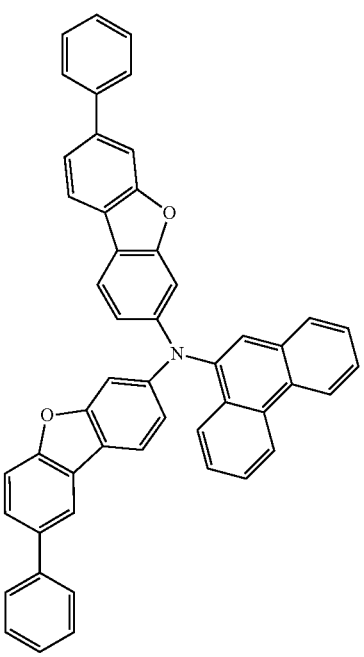

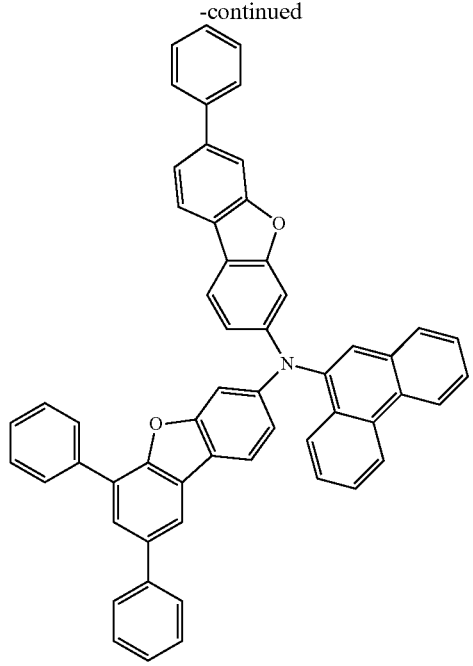
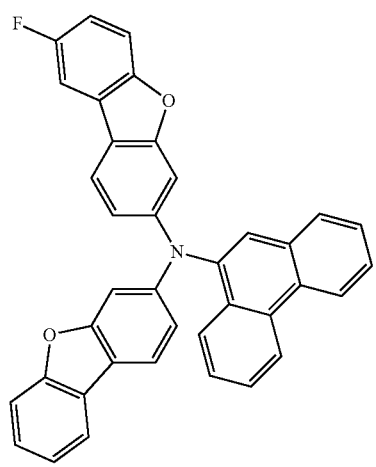
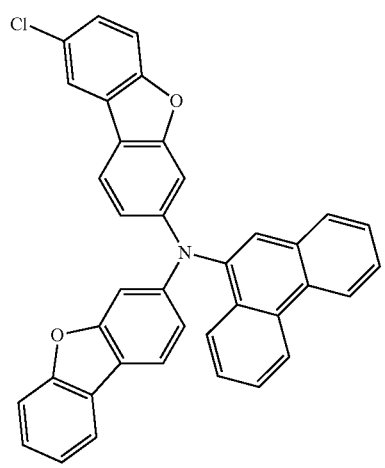
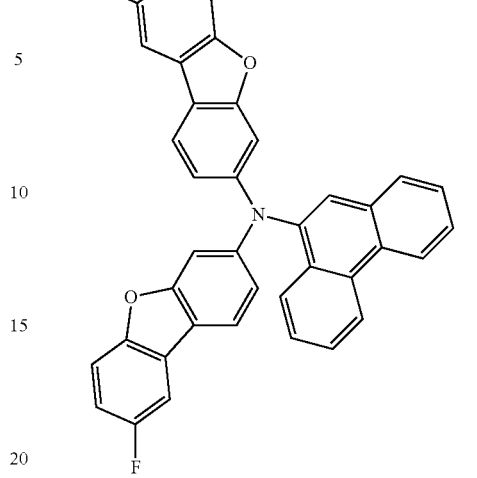
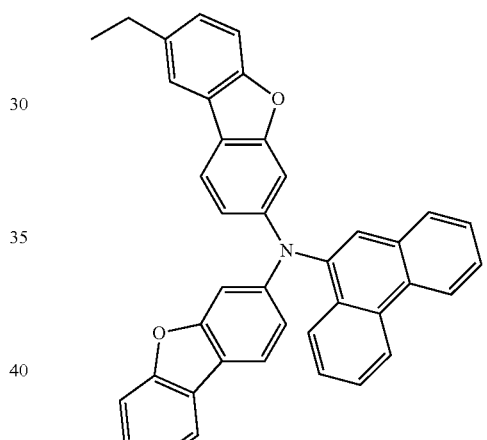
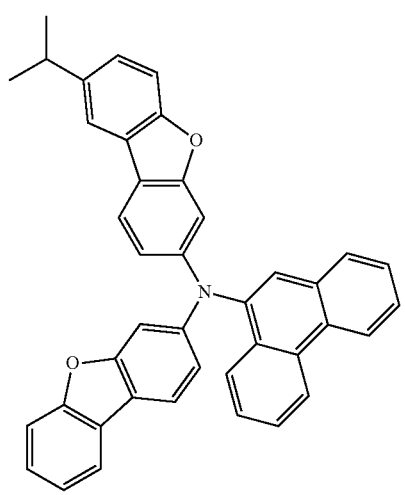

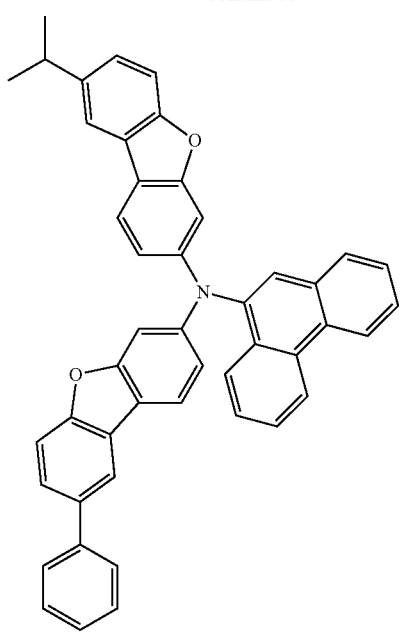
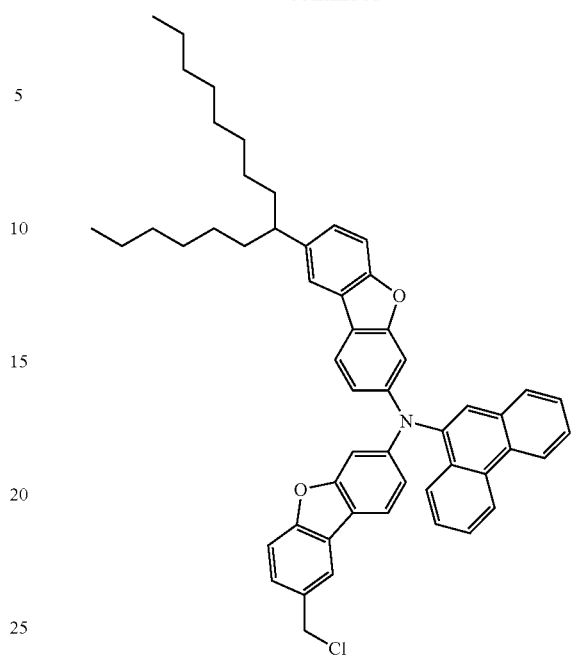
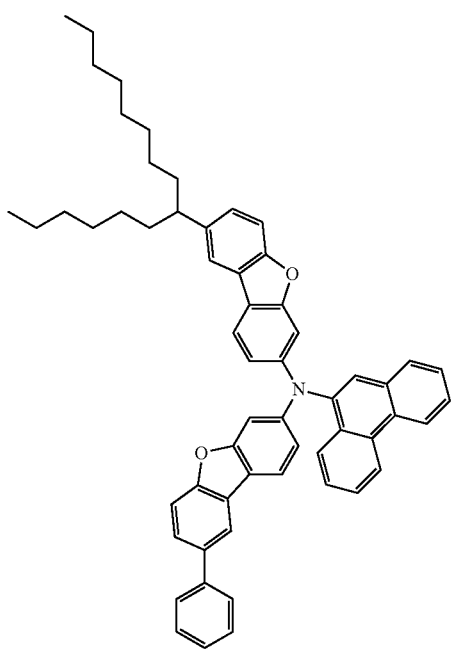
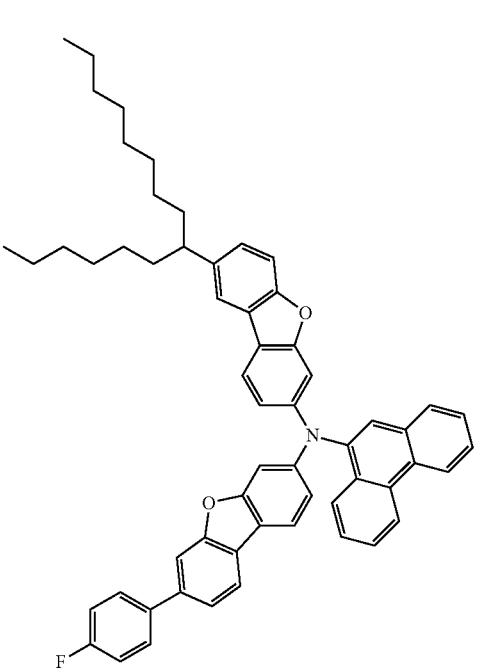

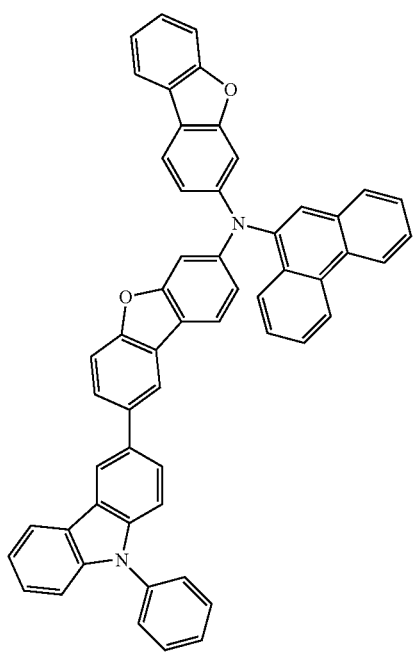
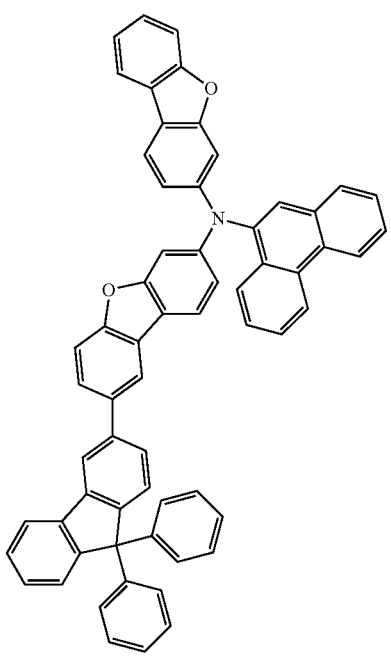
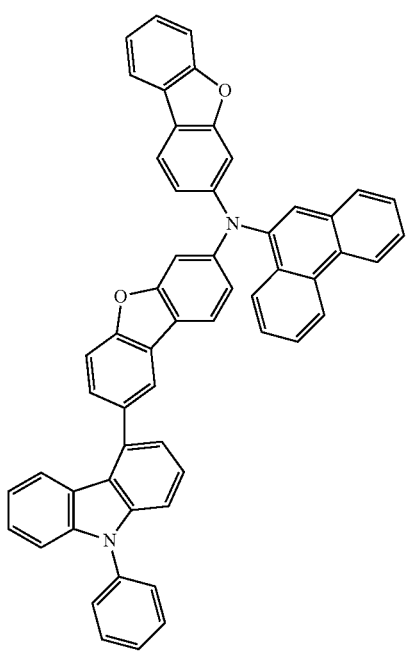
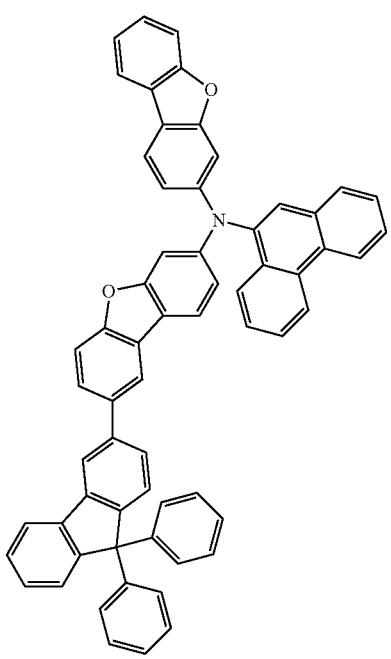

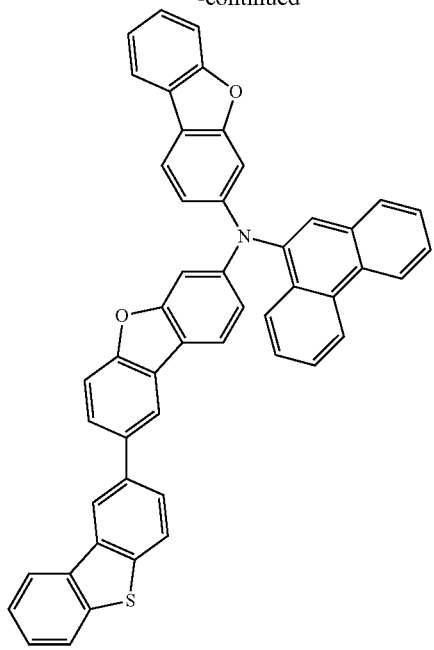
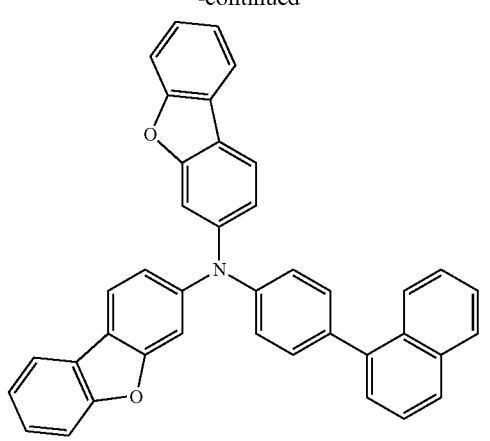
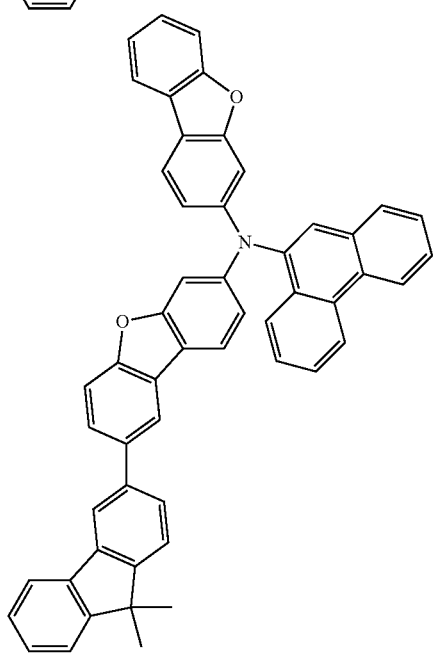
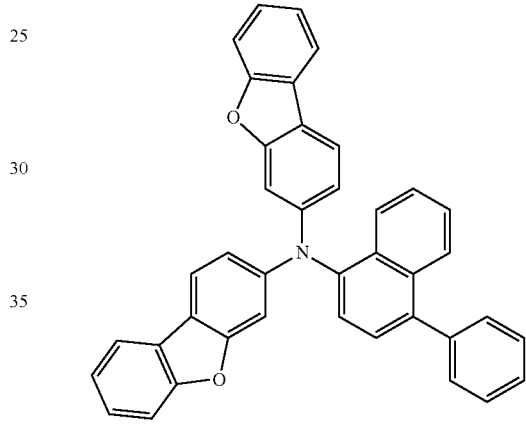
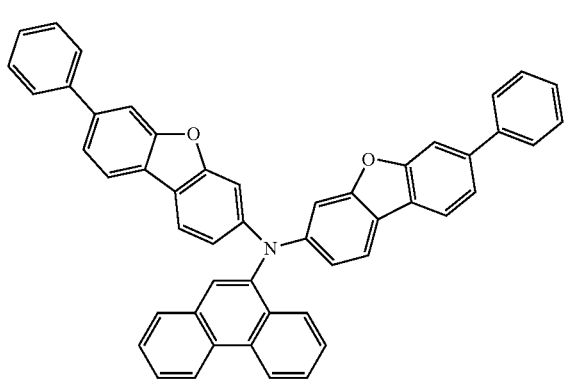
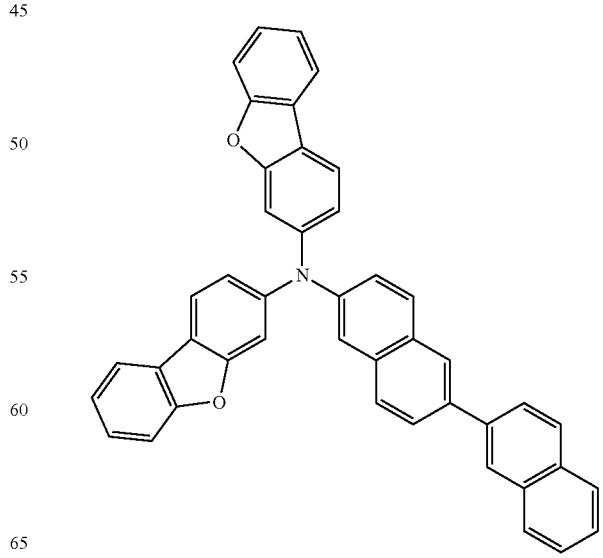

13
-continued
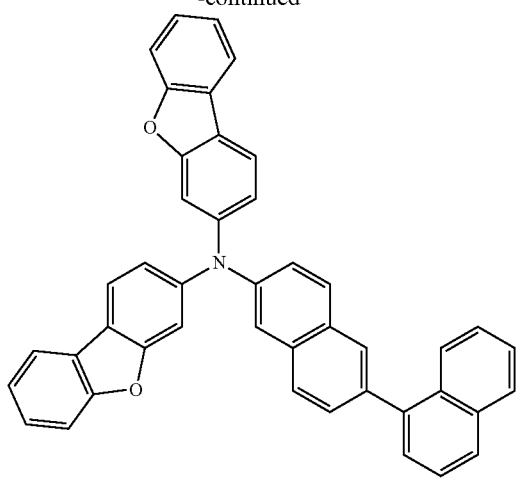
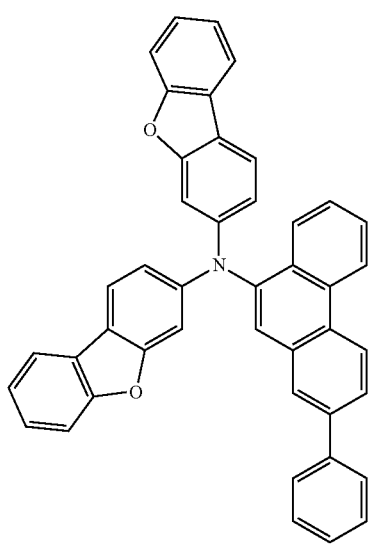
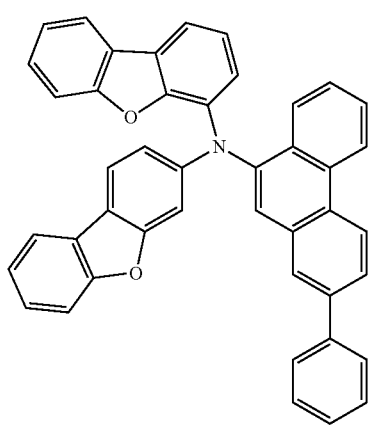
14
-continued
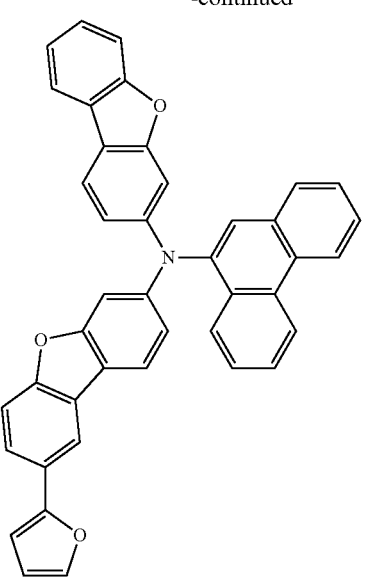
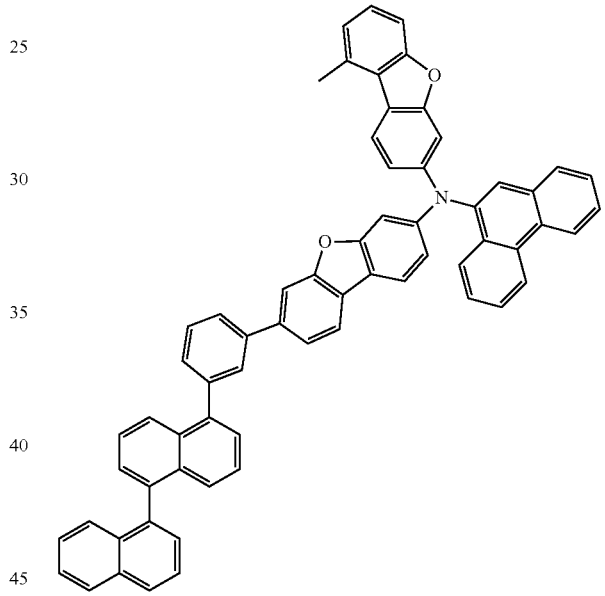
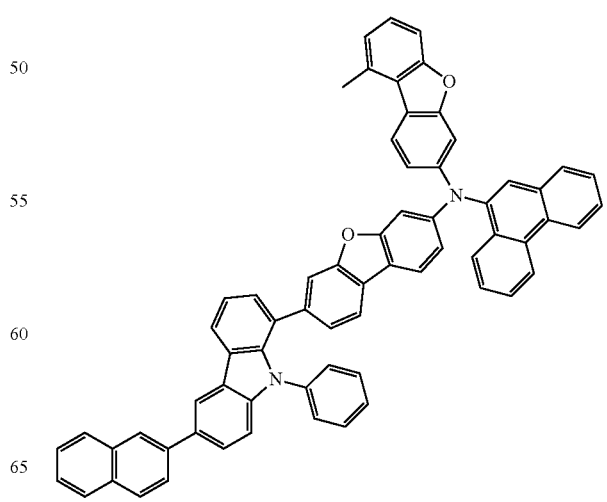

-continued
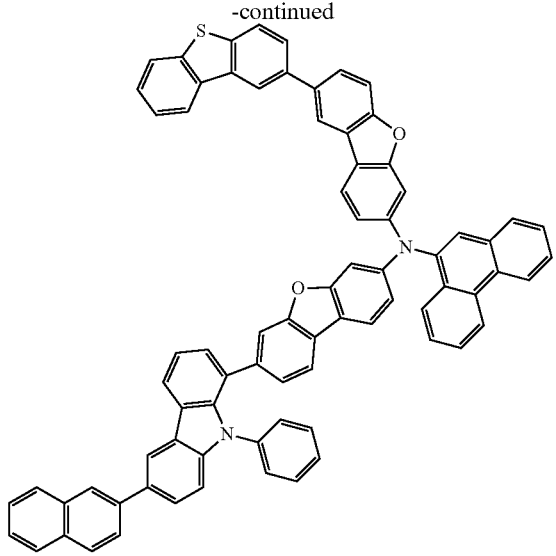
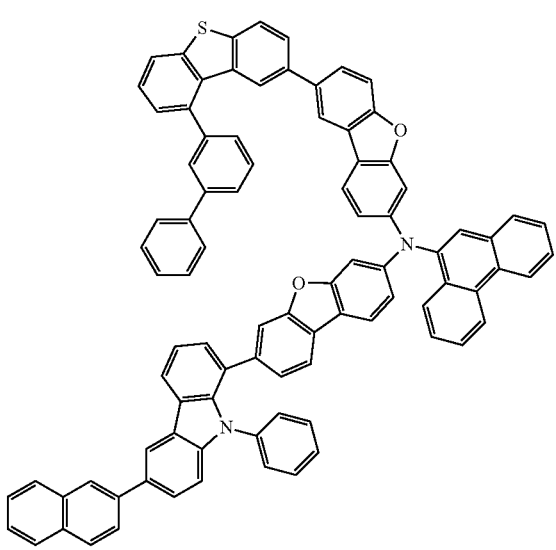
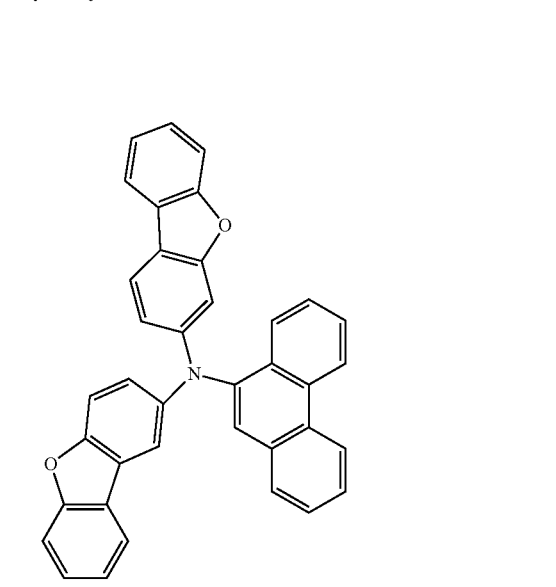
-continued
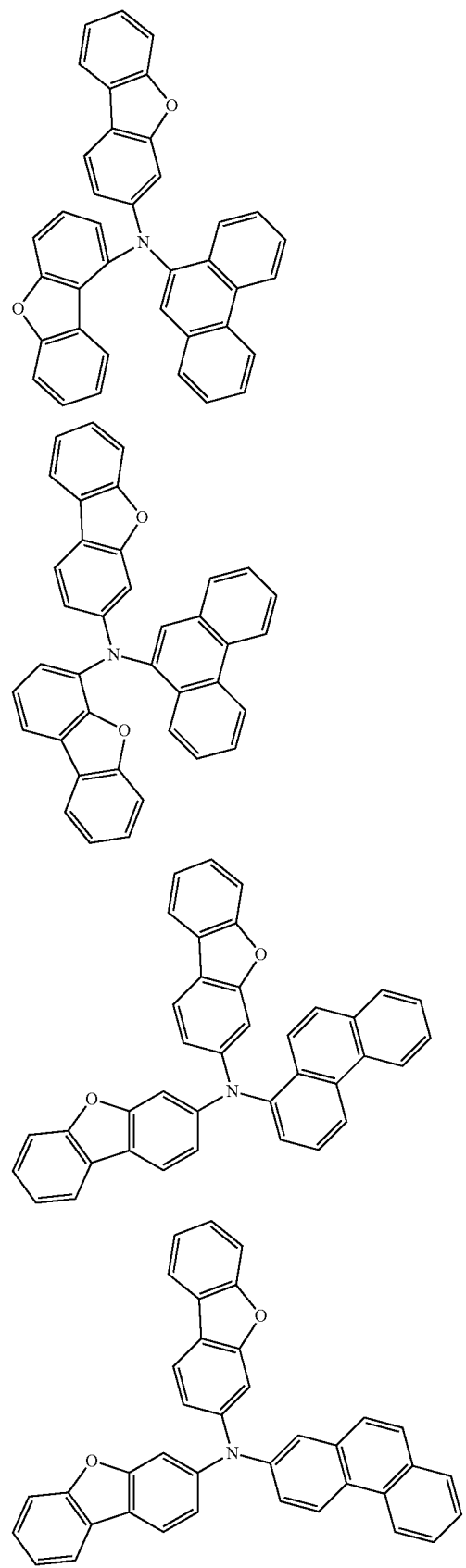

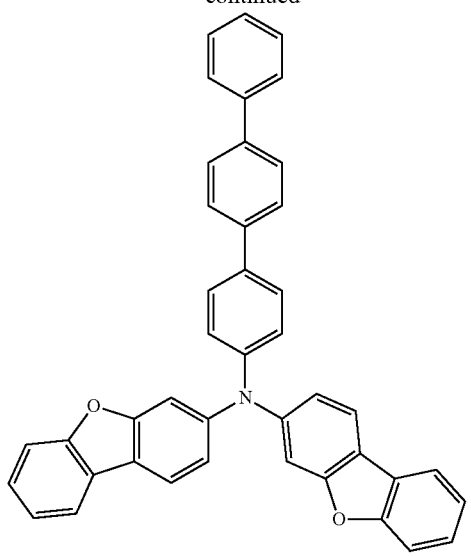
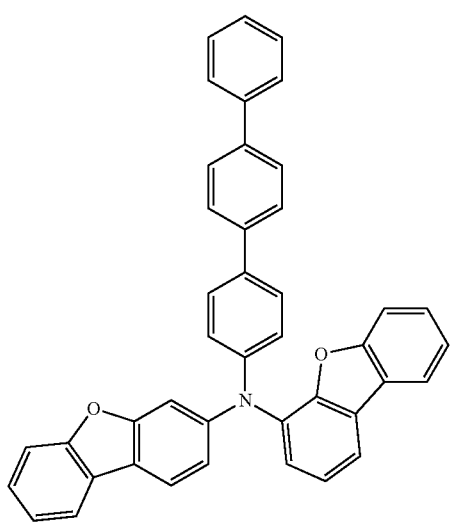
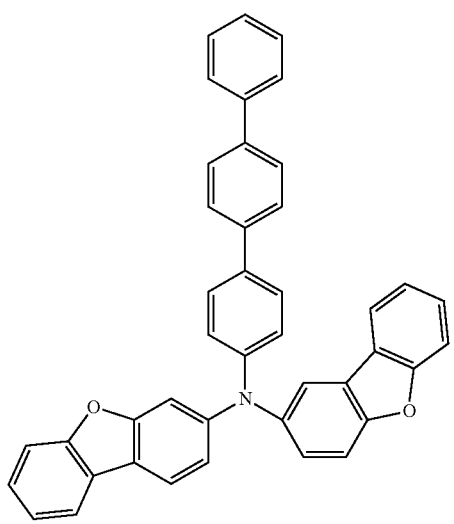
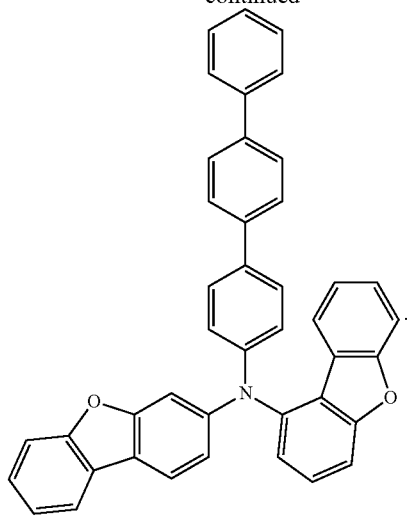

The embodiments may be realized by providing an organic electroluminescent device including a material for an organic electroluminescent device, wherein the material for an organic electroluminescent device includes a monoamine compound represented by the following Formula 1:

[Formula 1]

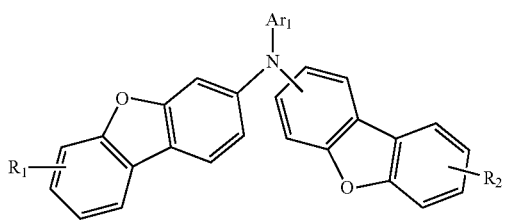

wherein, in Formula 1, $R_1$ and $R_2$ are each independently a hydrogen atom, a halogen atom, an alkyl group having 1 to 15 carbon atoms, a substituted or unsubstituted aryl group having 6 to 30 ring carbon atoms, or a substituted or unsubstituted heteroaryl group having 1 to 30 ring carbon atoms, and $Ar_1$ is represented by the following Formula 2, $$—(Ar_2)_l—(Ar_3)_m—Ar_4 \quad\quad \text{[Formula 2]}$$

wherein, in Formula 2, $Ar_2$, $Ar_3$, and $Ar_4$ are each independently a substituted or unsubstituted aryl group having 6 to 50 ring carbon atoms, and l+m is an integer from 0 to 2.

The material for an organic electroluminescent device may be included in a hole transport layer.

The compound represented by Formula 1 may include one of the following compounds:

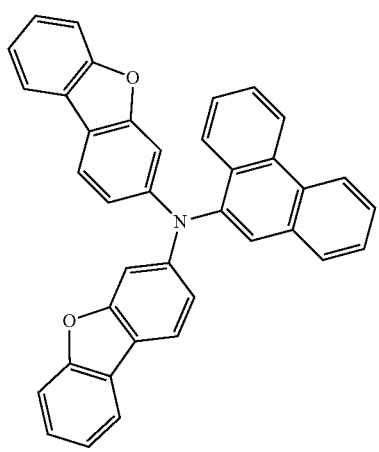
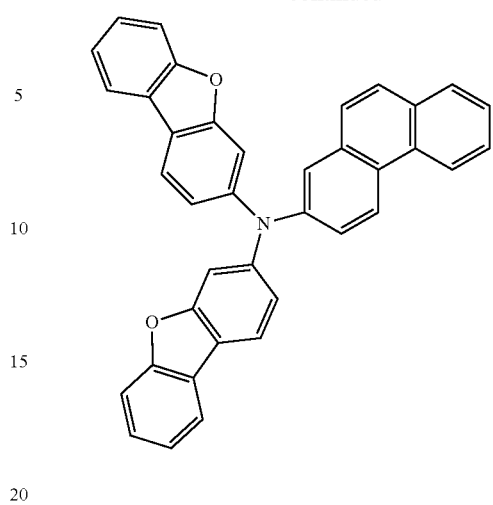
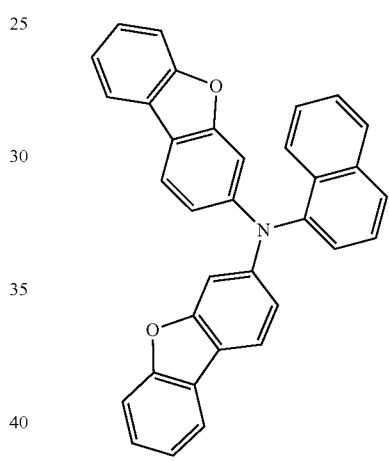
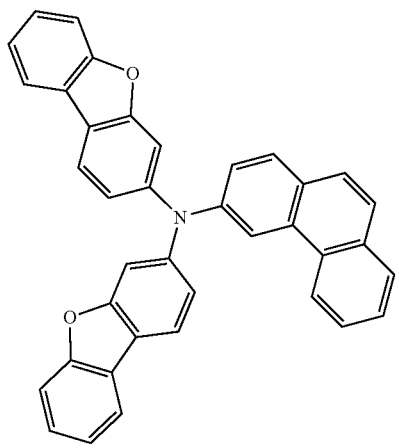
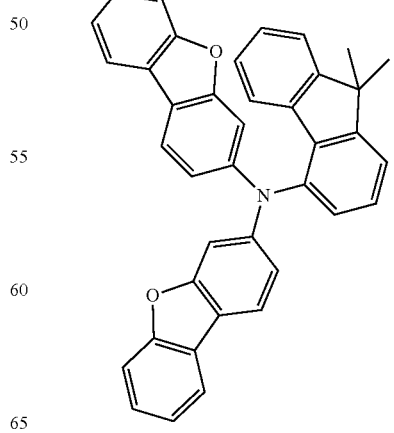

-continued
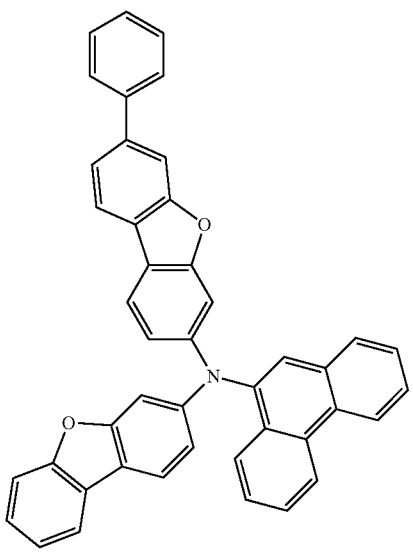
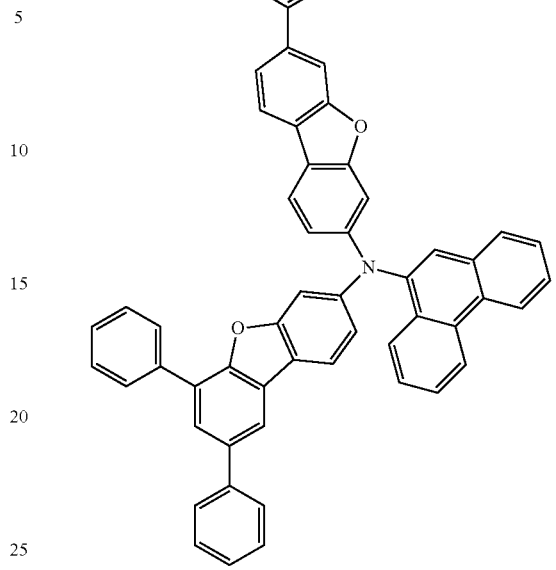
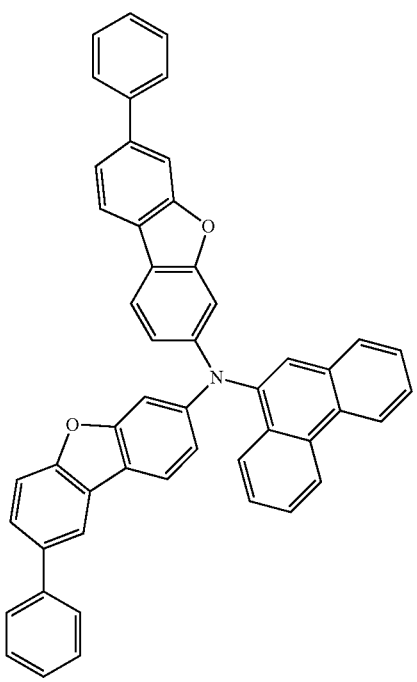
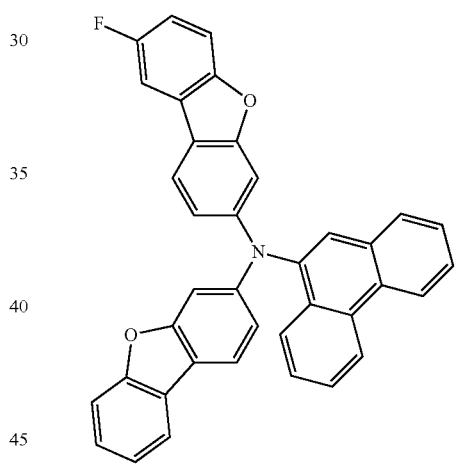
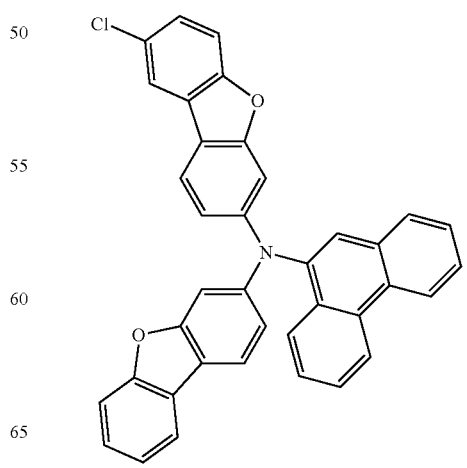

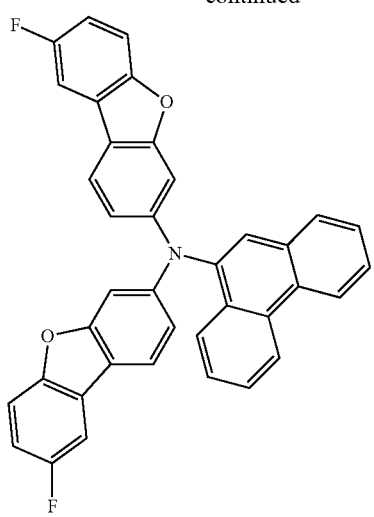
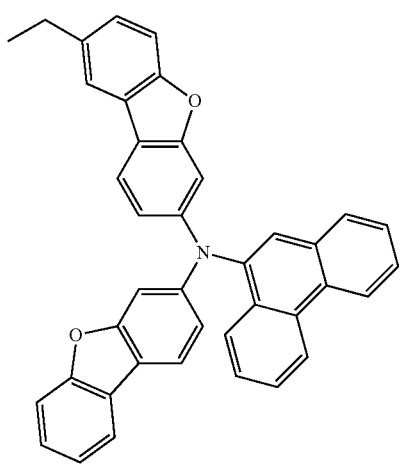
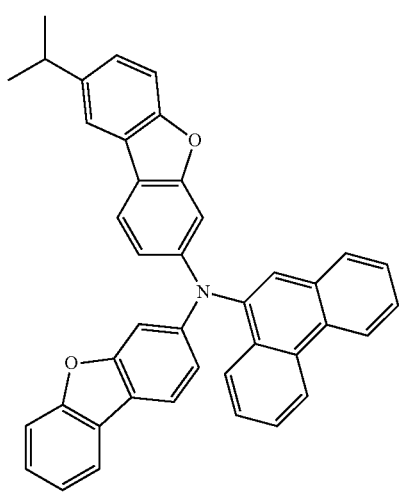
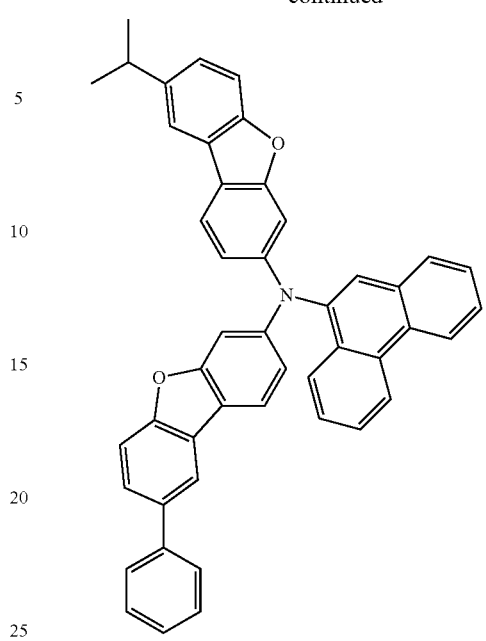
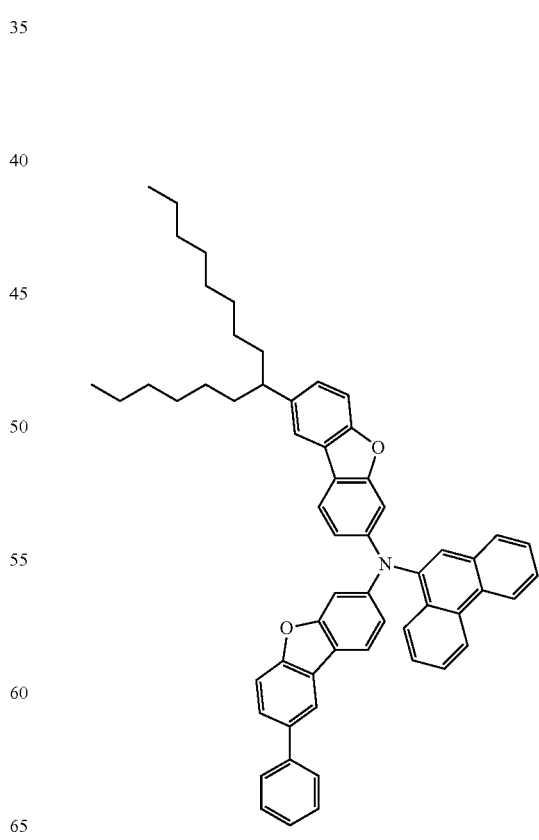

25
-continued
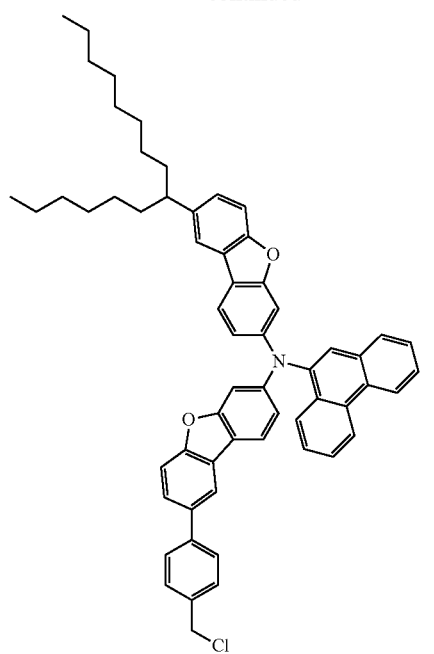
26
-continued
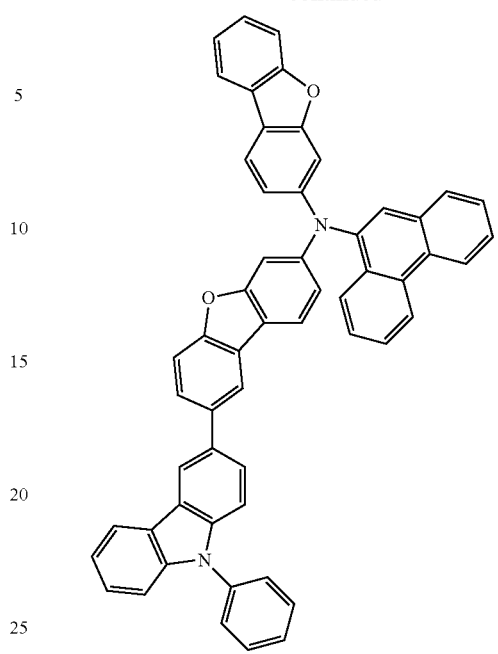
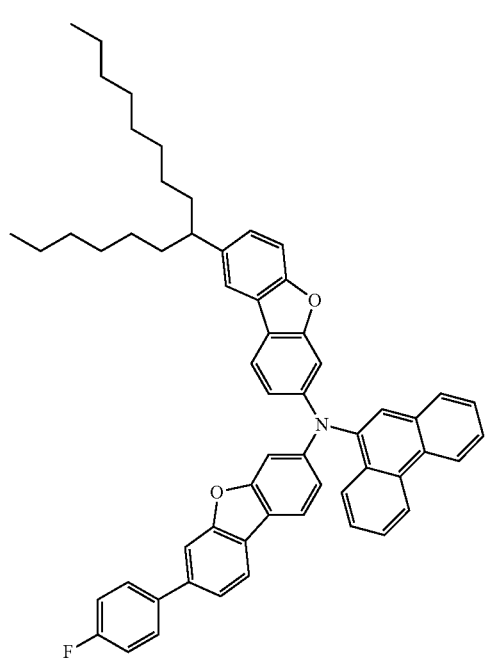
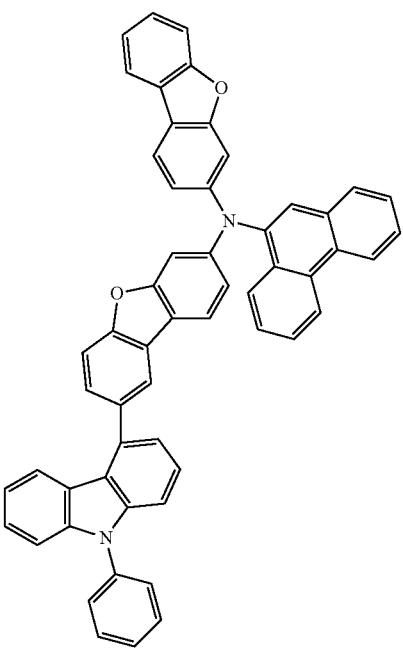

27
-continued
28
-continued
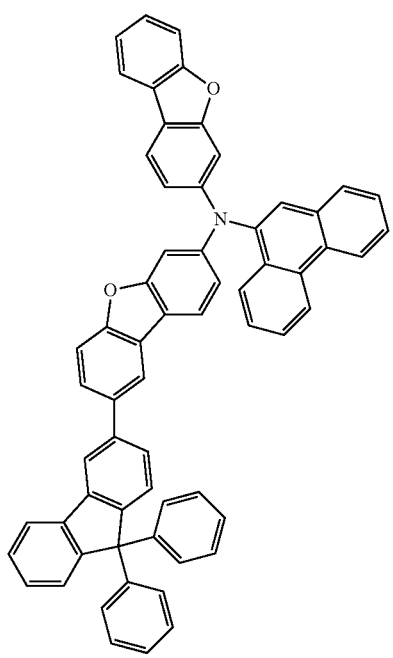
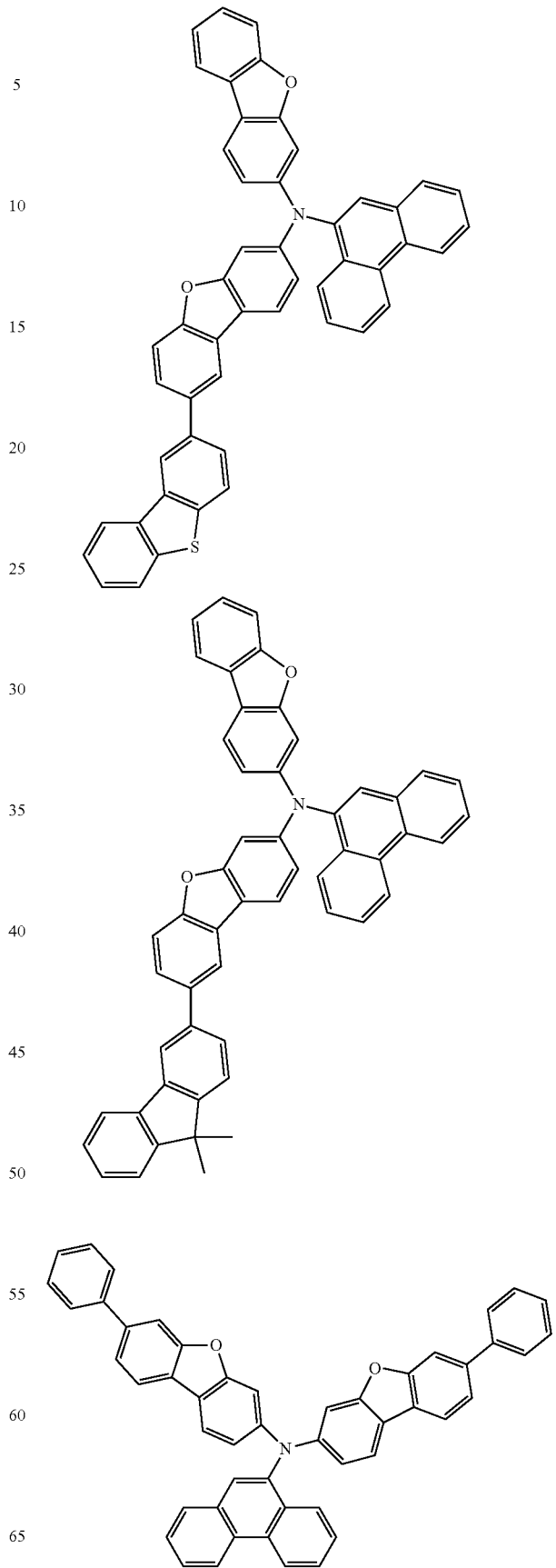

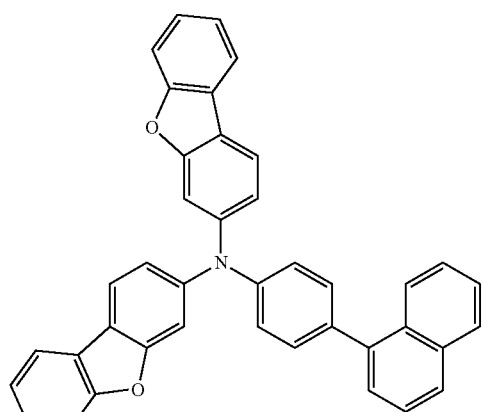
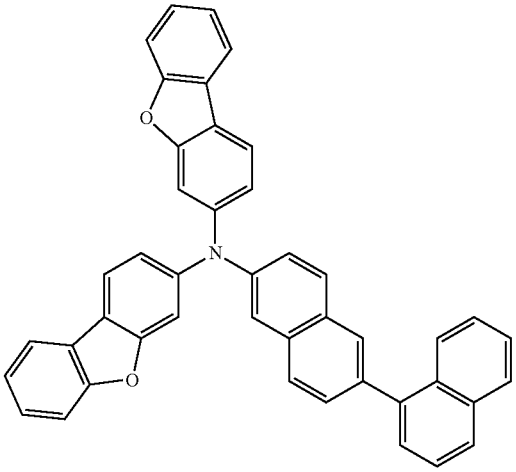
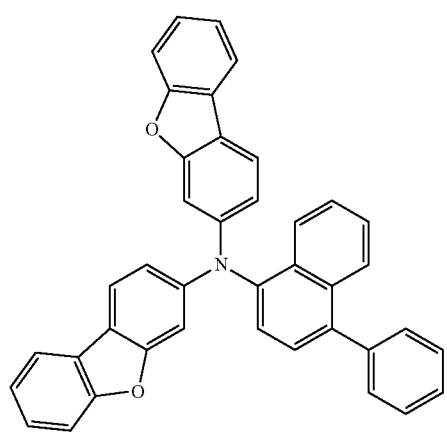
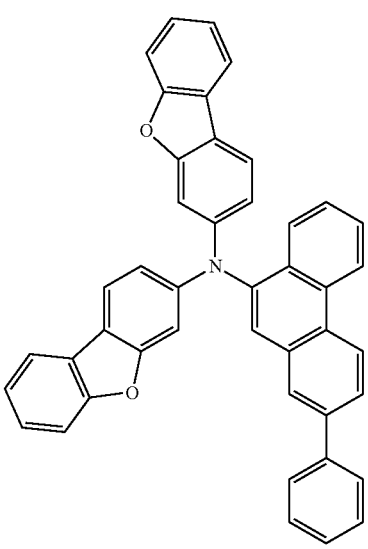
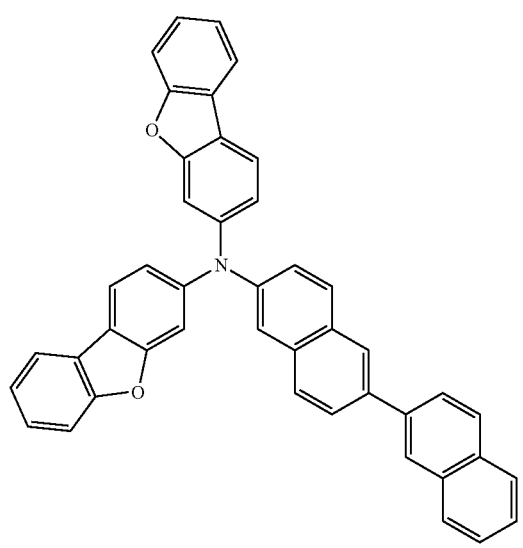
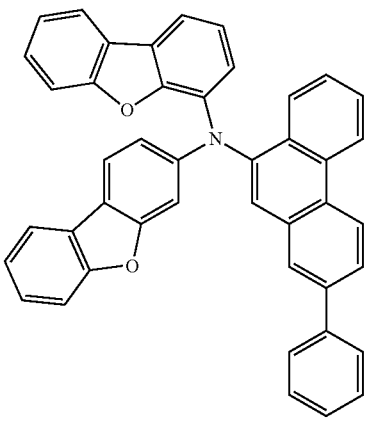

31
-continued
32
-continued
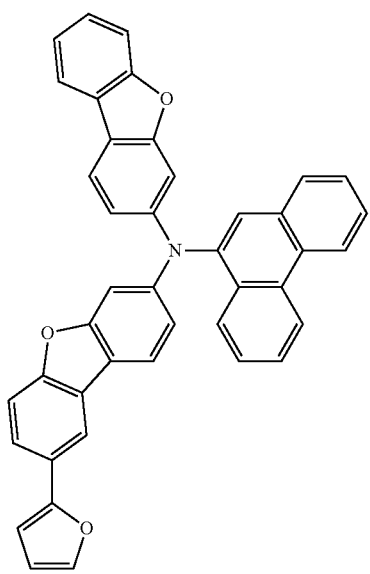
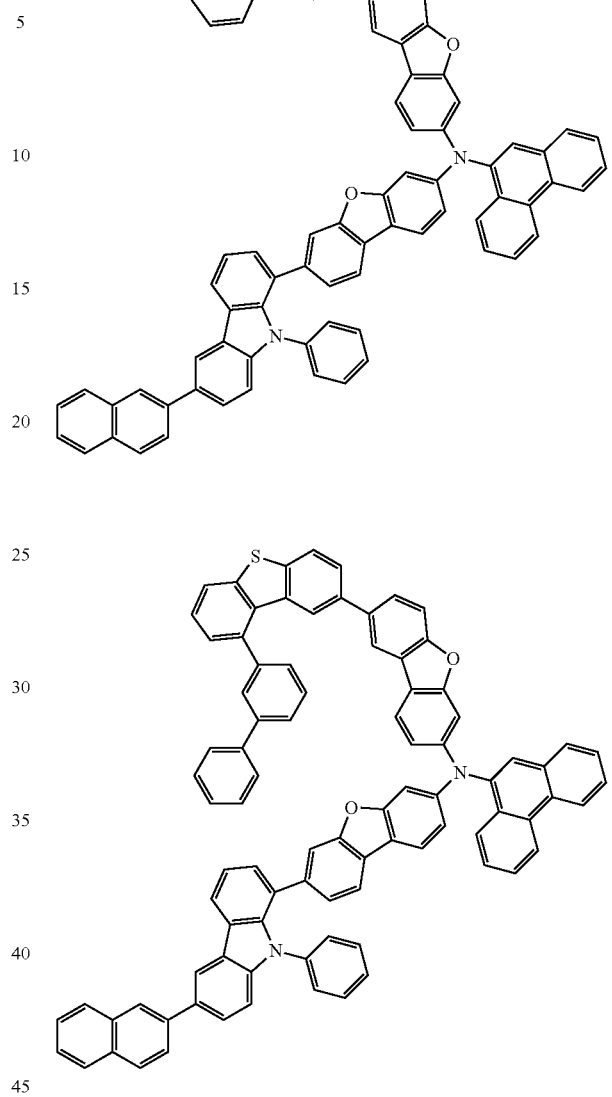
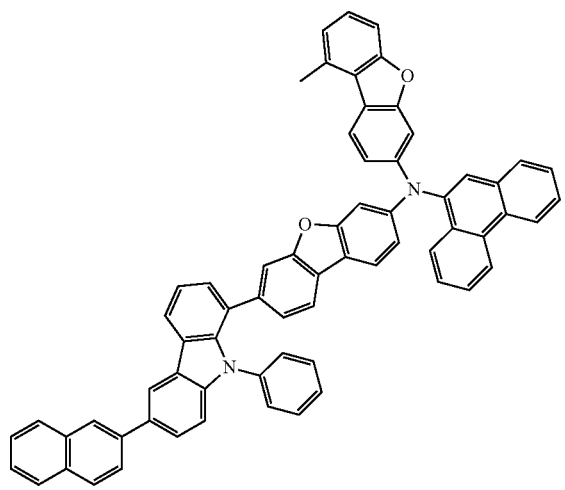
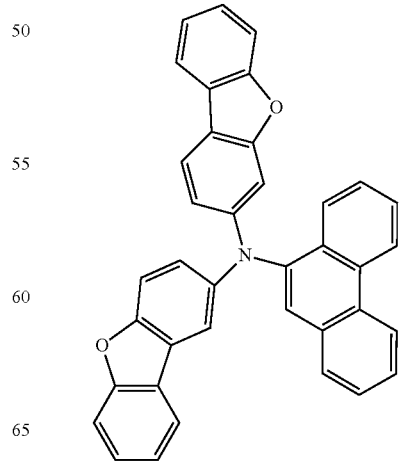

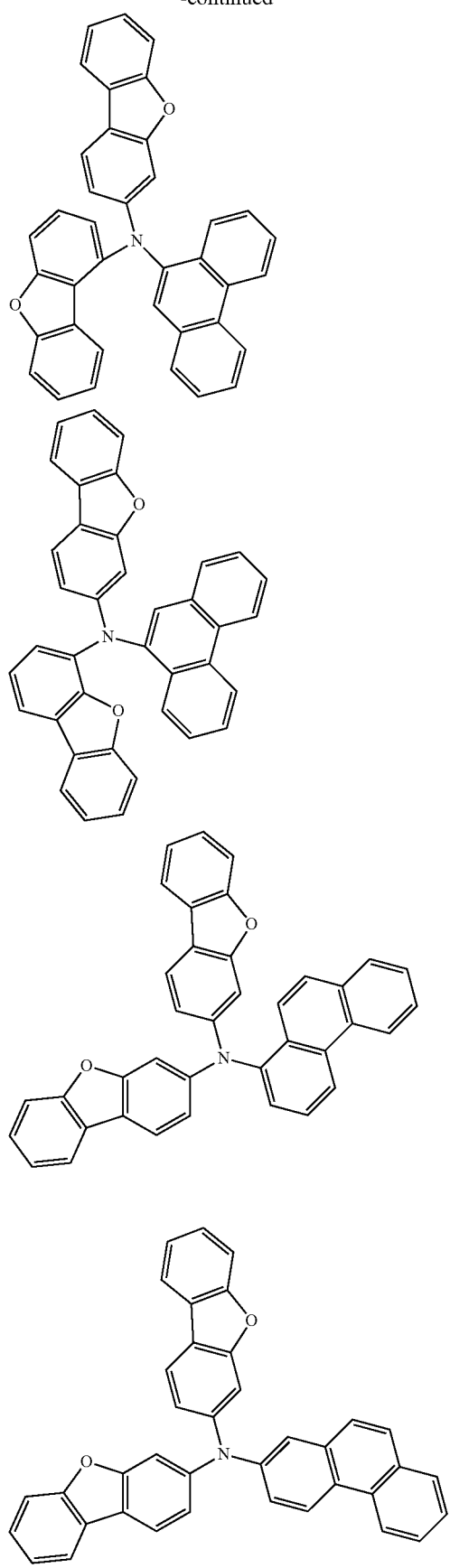
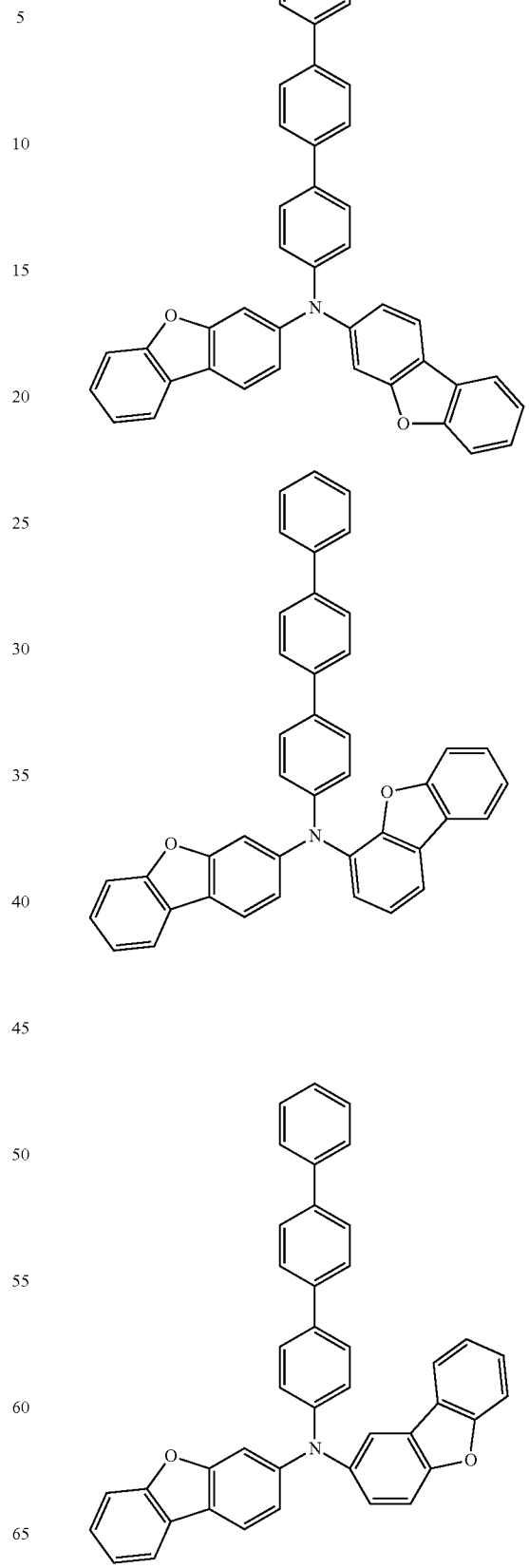

-continued

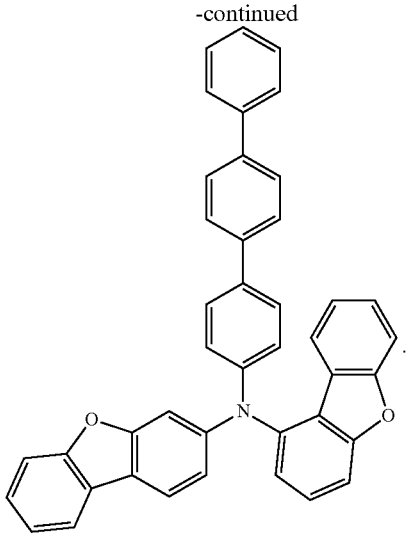

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
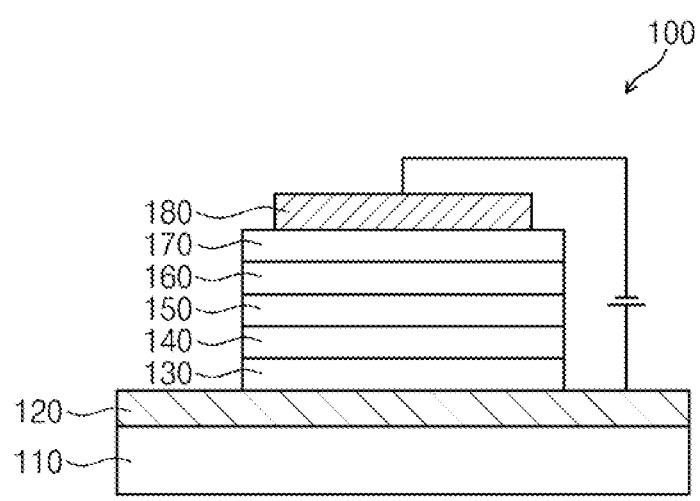
FIG. 1 illustrates a schematic cross-sectional view of an organic electroluminescent device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or element, it can be directly on the other element, or intervening elements may also be present. In addition, it will also be understood that when an element is referred to as being "between" two elements, it can be the only element between the two elements, or one or more intervening elements may also be present. Like reference numerals refer to like elements throughout.

<1. Configuration of Material for Organic Electroluminescent Device>

Materials for an organic electroluminescent device according to an embodiment may help improve the emission life of an organic electroluminescent device. For example, when using the material for an organic electroluminescent device according to an embodiment as a hole transport material, the emission life of the organic electroluminescent device may be improved. Here, the configuration of the material for an organic electroluminescent device according to an embodiment will be explained. The material for an organic electroluminescent device according to an embodiment of may include, e.g., a monoamine compound represented by the following Formula 1.

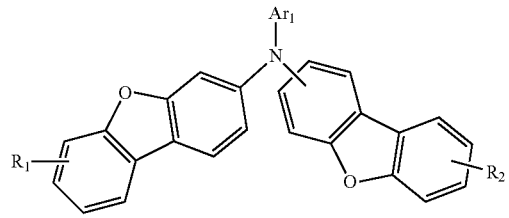

[Formula 1]

In Formula 1, $Ar_1$ may be or include a moiety represented by the following Formula 2.

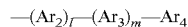

—$(Ar_2)_l$—$(Ar_3)_m$—$Ar_4$ [Formula 2]

In Formula 2, $Ar_2$, $Ar_3$ and $Ar_4$ may each independently be or include, e.g., a substituted or unsubstituted aryl group having 6 to 50 ring carbon atoms. l and m are integers, and l+m may be an integer of 0 to 2.

In an implementation, $Ar_1$ may be obtained by combining or condensing three substituted or unsubstituted phenyl groups. For example, $Ar_1$ may include three substituted or unsubstituted phenyl groups connected by a single bond (as in a terphenyl group), may include three fused substituted or unsubstituted phenyl groups (as in an anthracenyl group), or a combination thereof (as in a phenyl group singly bonded to a naphthyl group). For example, $Ar_1$ may include a phenyl group, a biphenyl group, a terphenyl group, a naphthyl group, an anthryl group, a phenanthryl group, a naphthalenylphenyl group, a fluorenyl group, an indenyl group, a pyrenyl group, a fluoranthenyl group, a triphenylenyl group, or the like. In an implementation, $Ar_1$ may include the phenyl group, the biphenyl group, the terphenyl group (e.g., a p-terphenyl group), the naphthyl group, the phenanthryl group, the naphthalenylphenyl group, and/or the triphenylenyl group.

The aryl group of $Ar_1$ may be substituted. In an implementation, the substituents may include an alkyl group (e.g., a methyl group, an ethyl group, etc.), an alkenyl group (e.g., a vinyl group, an allyl group, etc.), a halogen atom (e.g., a fluorine atom, a chlorine atom, etc.), a silyl group (e.g., a trimethylsilyl group), a cyano group, an alkoxy group (e.g., a methoxy group, a butoxy group, an octoxy group), a nitro group, a hydroxyl group, a thiol group, or the like, e.g., other than the aryl group. In an implementation, the substituent may include a functional group other than the vinyl group, the indolyl group, and the triphenylenyl group, in consideration of thermal stability. In an implementation, the substituents may further be substituted with the same types of substituents.

In an implementation, in a case in which $Ar_1$ includes a phenanthrenyl group, the glass transition temperature may be unusually high for the molecular weight of the monoamine compound. Thus, the thermal stability of the molecule thereof may be increased, and a layer quality may be improved. Therefore, in the case that $Ar_1$ includes the phenanthrenyl group, the emission life of the organic electroluminescent device may be largely improved. In an implementation, a phenanthrenyl group may form an aromatic ring with other atoms (e.g., a heteroatom such as a nitrogen atom).

In an implementation, in a case in which $Ar_1$ does not include the phenanthrenyl group, the emission life may still be increased. For example, in the case that the emission life may be increased even when $Ar_1$ is a substituent obtained by combining or condensing three phenyl groups (a terphenyl group, a naphthalenylphenyl group, etc.). In 3-substituted dibenzofuran which is the essential structure of the monoamine compound, m position of a heteroatom of oxygen may be combined with or bound to nitrogen. Thus, even if $Ar_1$ does not include the phenanthrenyl group, the emission life may still be increased.

In Formula 1, $R_1$ and $R_2$ may each independently be or include, e.g., a hydrogen atom, a halogen atom (e.g., a fluorine atom, a chlorine atom, etc.), an alkyl group having 1 to 15 carbon atoms, a substituted or unsubstituted aryl group having 6 to 30 ring carbon atoms, or a substituted or unsubstituted heteroaryl group having 1 to 30 ring carbon atoms.

The alkyl group having 1 to 15 carbon atoms may be, e.g., a linear type (e.g., a methyl group, an ethyl group, a propyl group, a butyl group, an octyl group, a decyl group, a pentadecyl group, etc.) or a branched type (e.g., a t-butyl group, etc.).

The aryl group having 6 to 30 ring carbon atoms may include an aryl group having 6 to 30 ring carbon atoms among the above-described aryl groups. The heteroaryl group having 1 to 30 ring carbon atoms may include a heteroaryl group having 4 to 30 ring carbon atoms among the above-described heteroaryl groups. In an implementation, the heteroaryl group may include, e.g., a tetrazolyl group, an imidazolyl group, a pyrazolyl group, an oxazolyl group, an isooxazolyl group, a thiazolyl group, an isothiazolyl group, or the like. The substituent of the aryl group and the heteroaryl group may be the same as the above-described substituent of the aryl group and the heteroaryl group of $Ar_1$.

In an implementation, as shown in Formula 1, at least one of the dibenzofuranyl groups making a direct linkage with the central nitrogen atom of the monoamine may be combined with or bound to the nitrogen atom at position 3 of the dibenzofuranyl group. In an implementation, all (e.g., both) dibenzofuranyl groups making a direct linkage with the nitrogen atom may be combined with or bound to the nitrogen atom at position 3. In this case, the emission life of the organic electroluminescent device may be further improved.

The material for an organic electroluminescent device according to an embodiment may be included in at least one of a hole transport layer and an emission layer, among layers constituting an organic electroluminescent device. In an implementation, the material for an organic electroluminescent device may be included in the hole transport layer.

The organic electroluminescent device using or including the material for an organic electroluminescent device having the above-mentioned configuration may exhibit improved emission life, as described in the following embodiments. In an implementation, the compound represented by Formula 1 may include one of the following compounds.

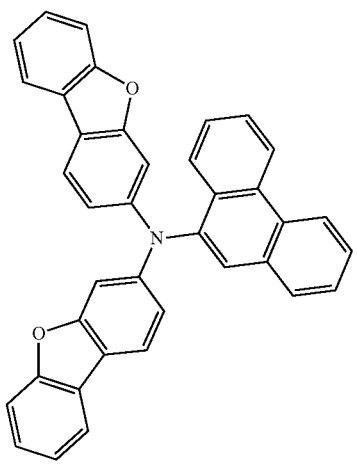

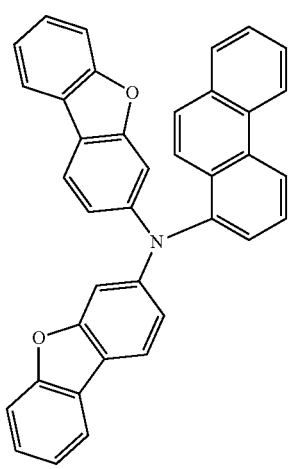

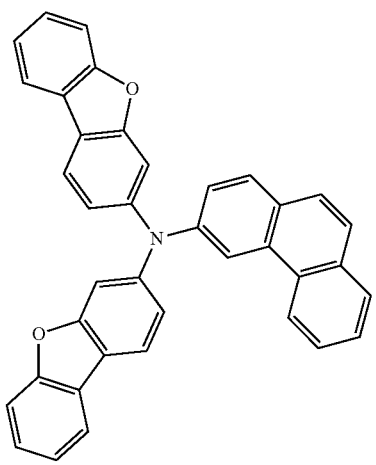

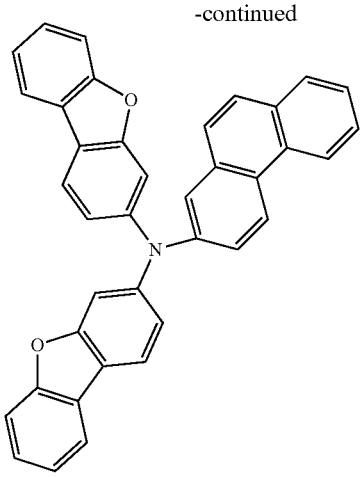
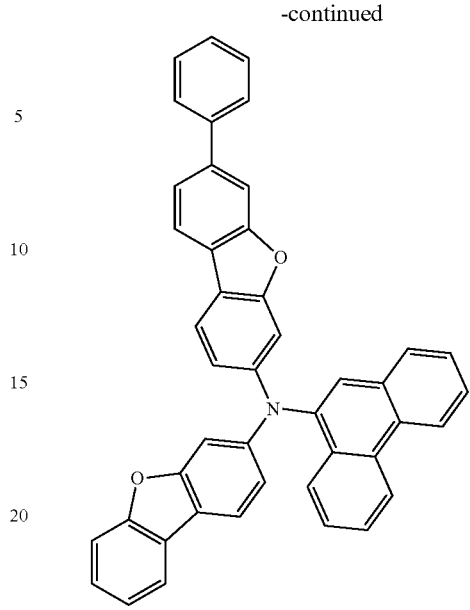
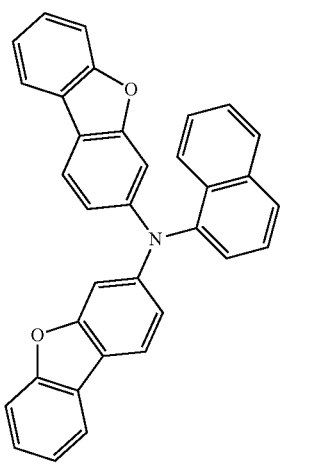
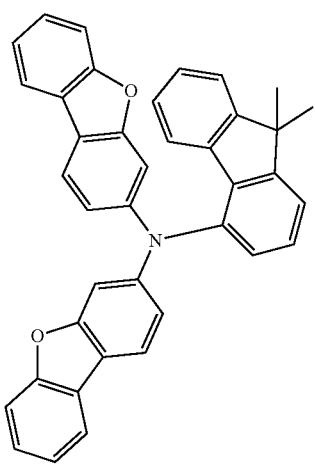

41
-continued
42
-continued
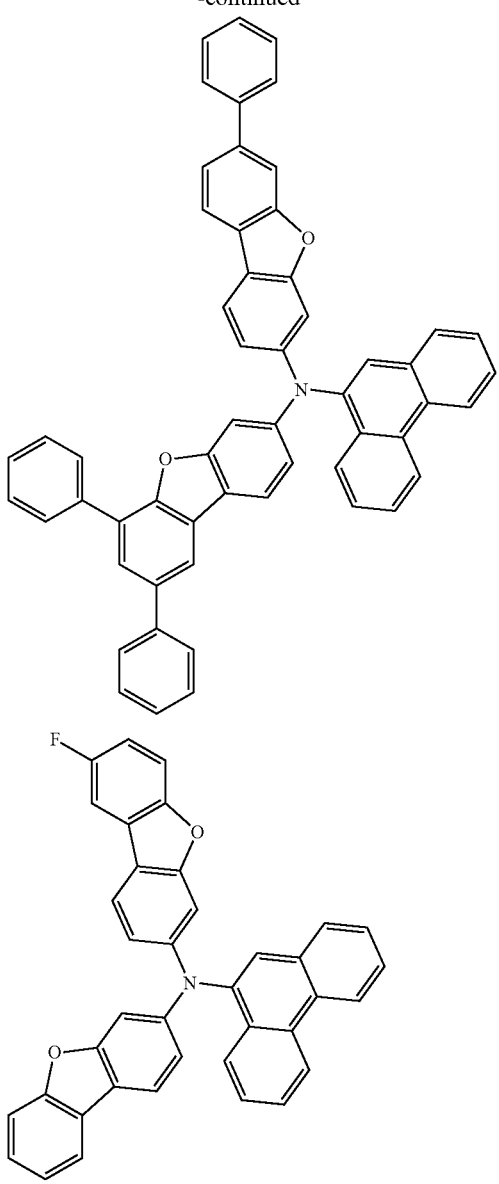
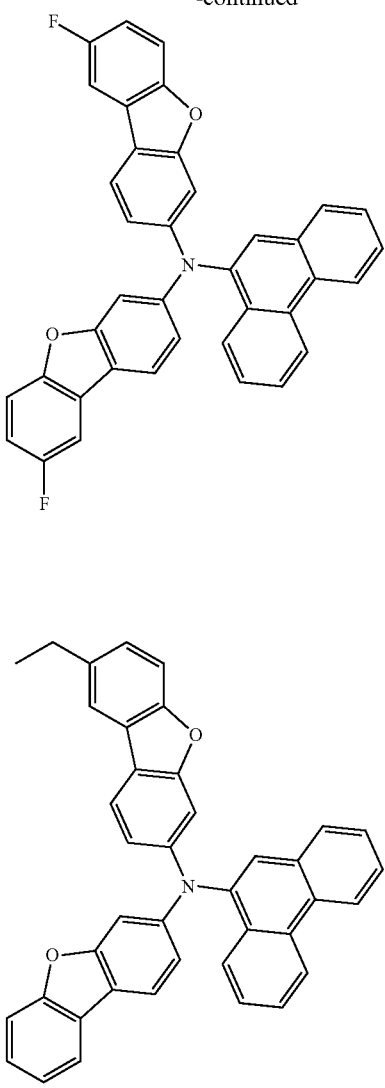
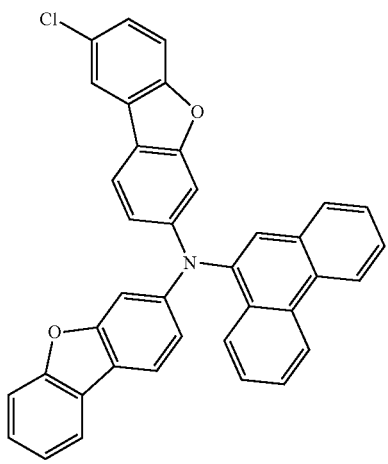

43
-continued
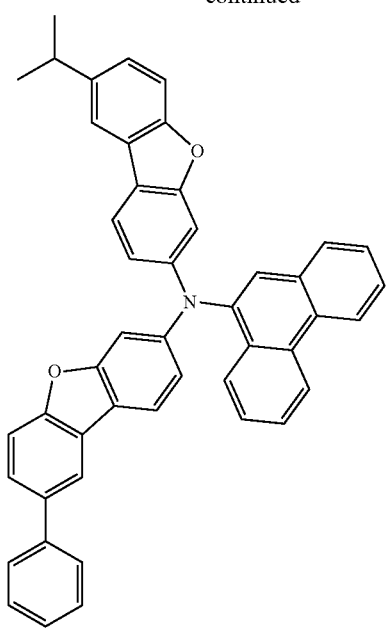
44
-continued
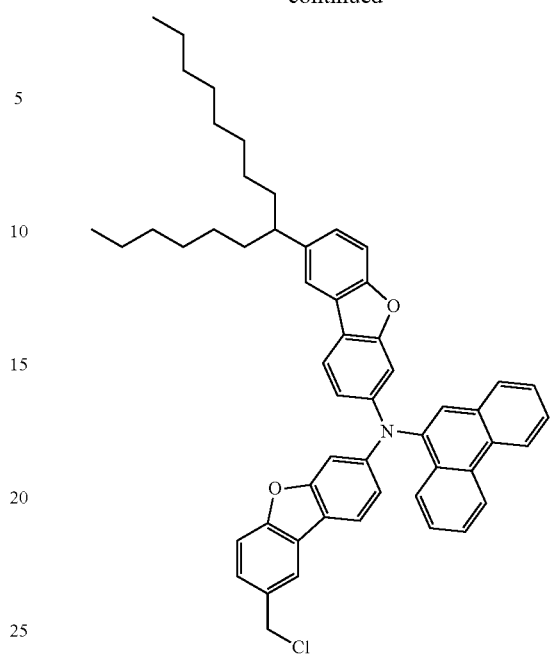
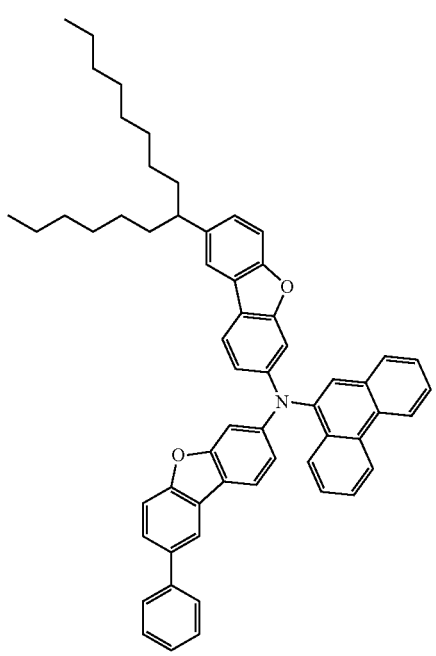
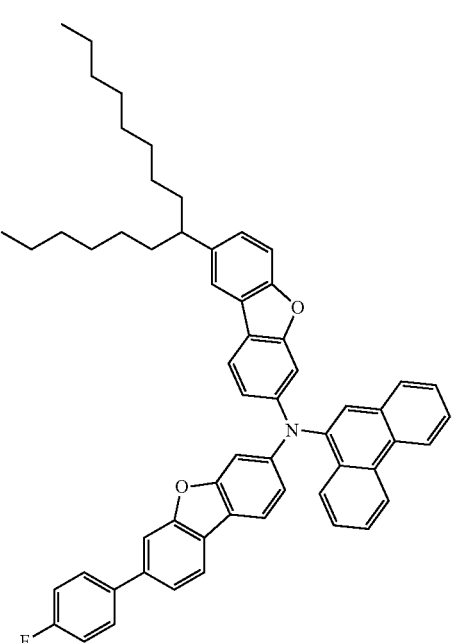

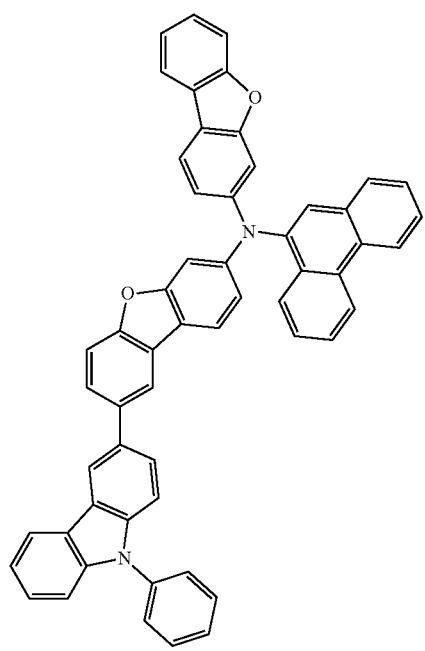
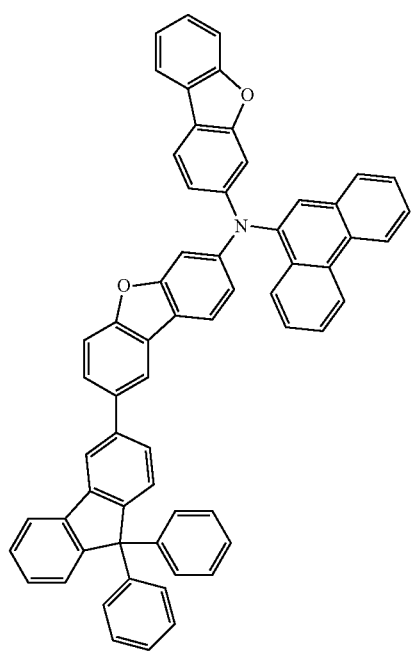
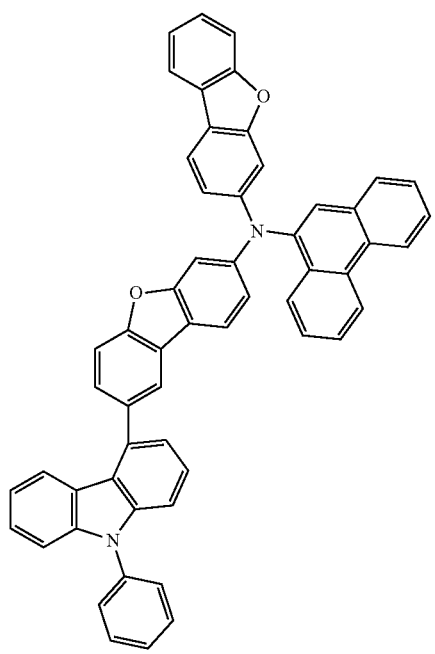
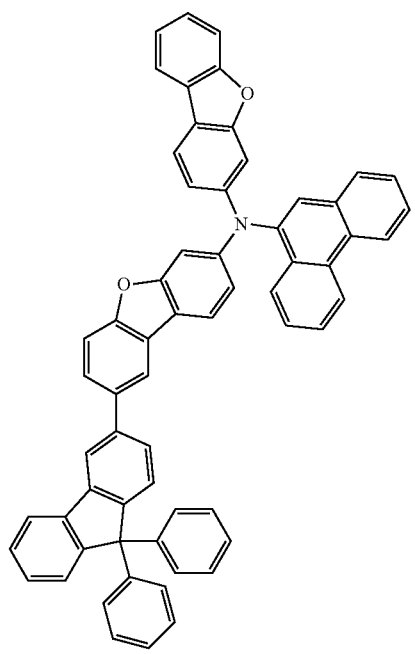

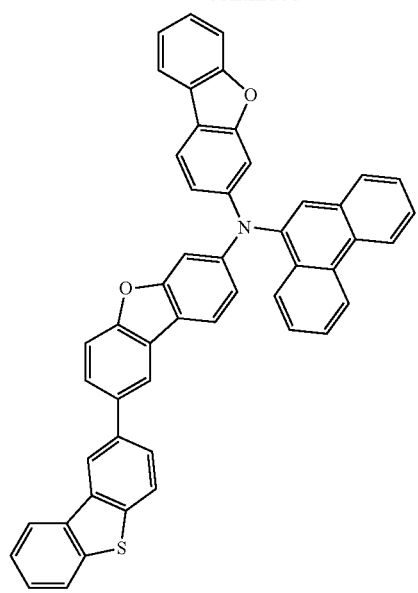
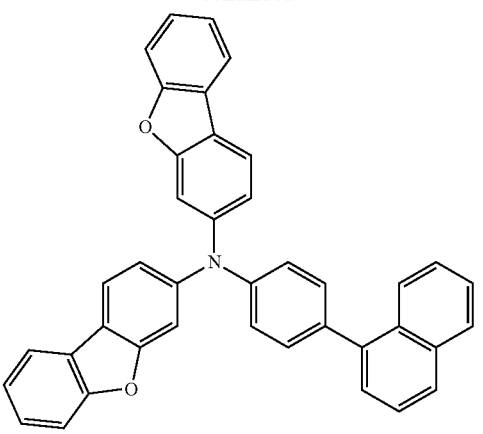
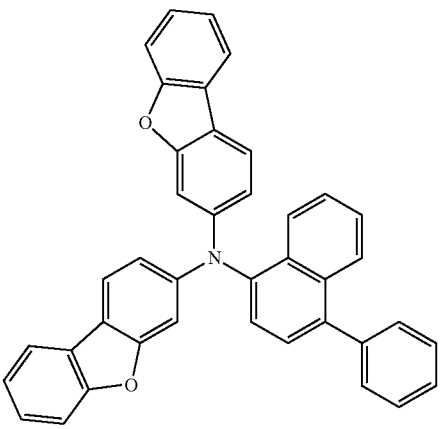
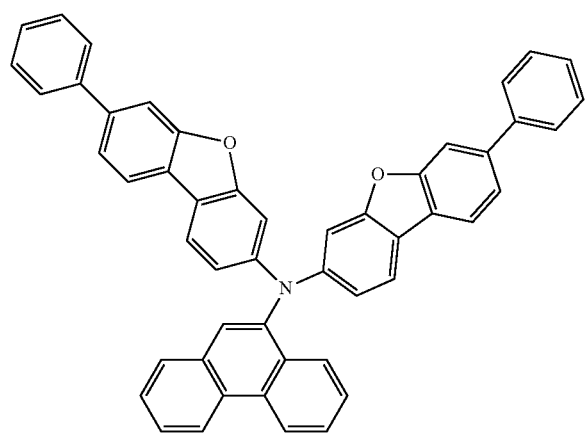

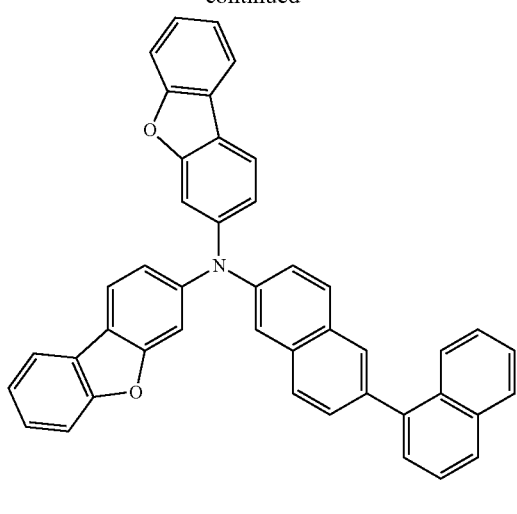
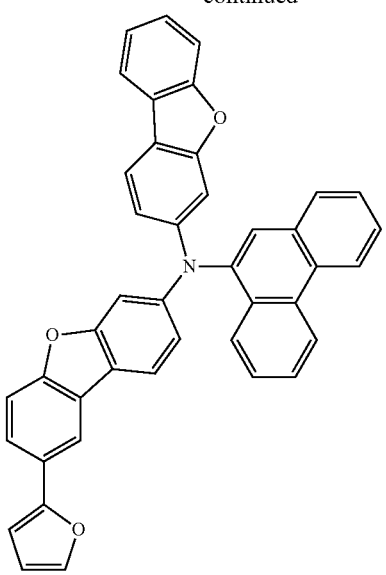
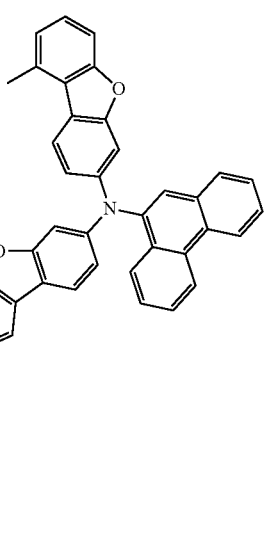
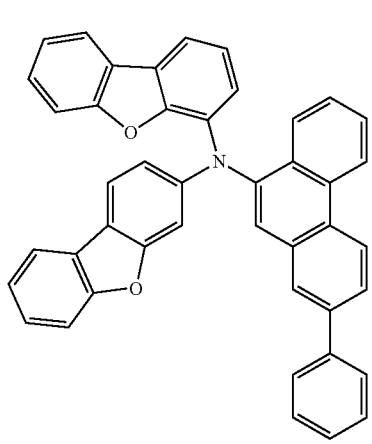
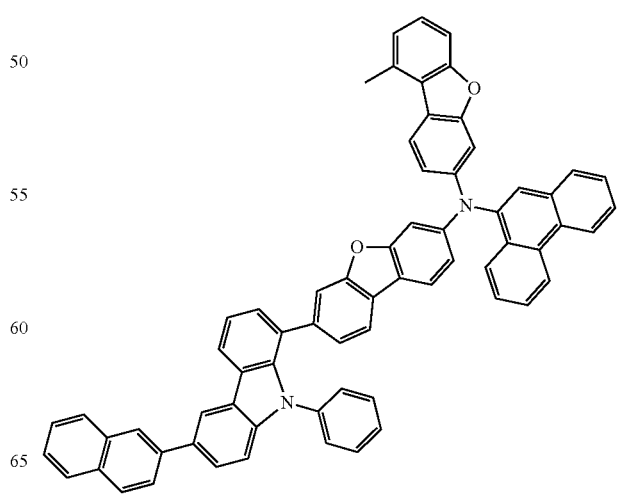

51
-continued
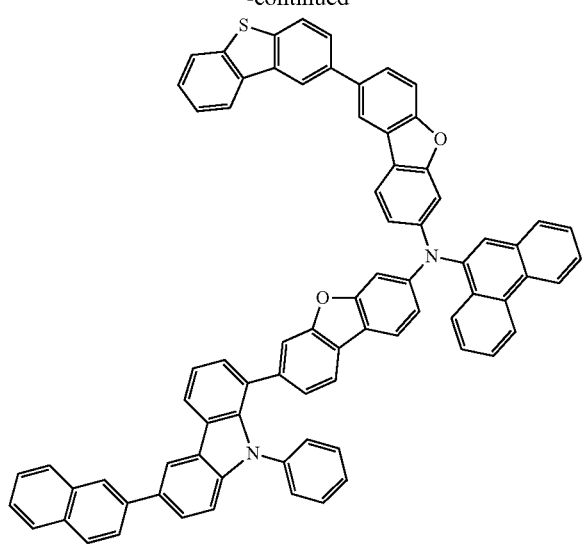
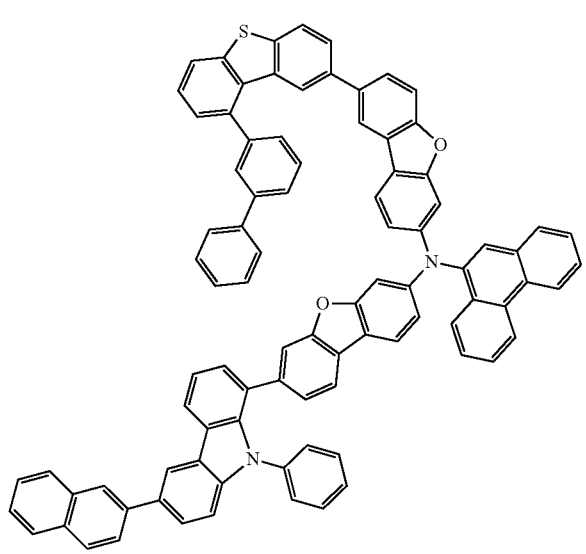
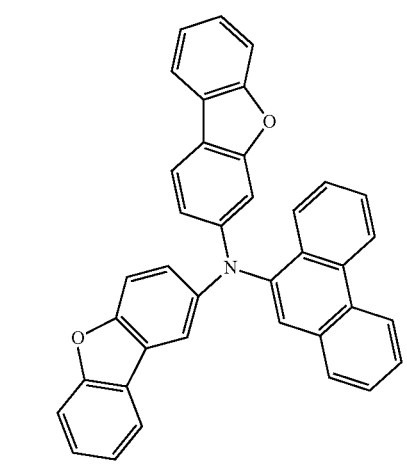
52
-continued
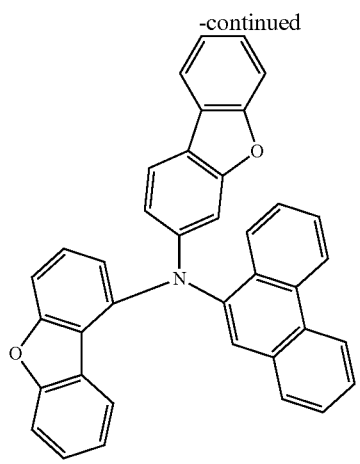
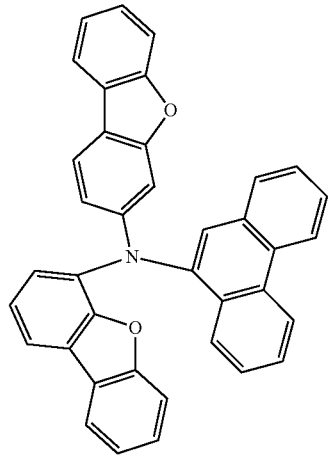
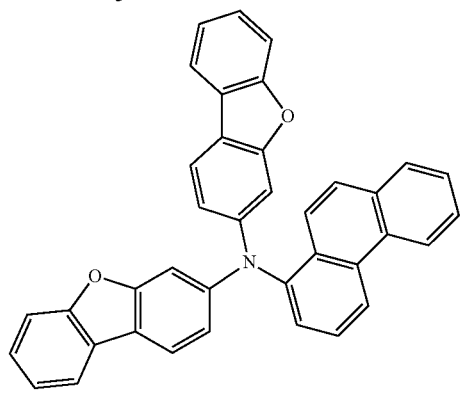
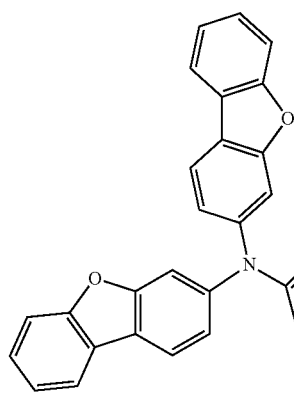

-continued

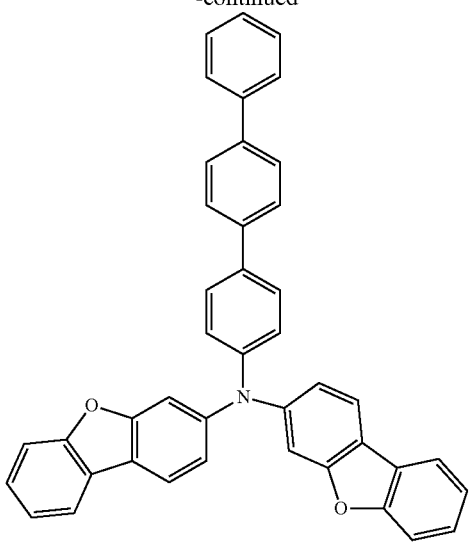

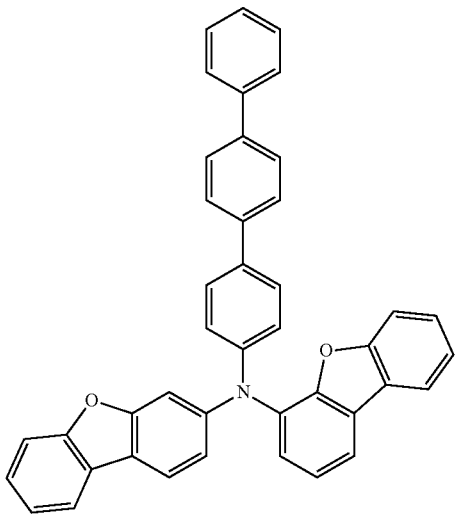

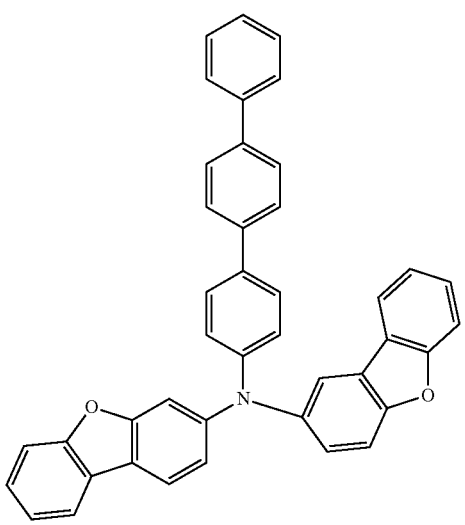

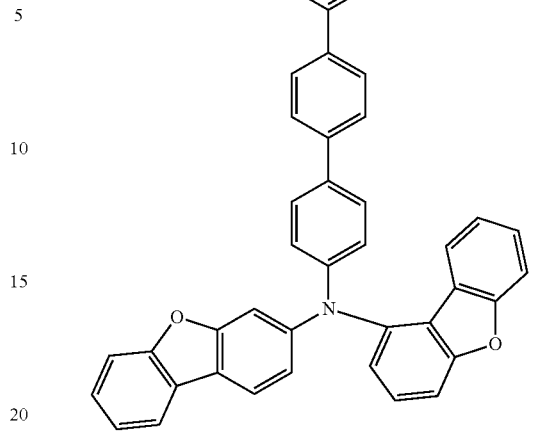

<2. Organic Electroluminescent Device Using Material for Organic Electroluminescent Device>

Referring to FIG. 1, the organic electroluminescent device including or using the material for an organic electroluminescent device according to an embodiment will be described in brief. FIG. 1 illustrates a schematic cross-sectional view of an organic electroluminescent device according to an embodiment.

As shown in FIG. 1, the organic electroluminescent device 100 according to an embodiment may include, e.g., a substrate 110, a first electrode 120 disposed on the substrate 110, a hole injection layer 130 disposed on the first electrode 120, a hole transport layer 140 disposed on the hole injection layer 130, an emission layer 150 disposed on the hole transport layer 140, an electron transport layer 160 disposed on the emission layer 150, an electron injection layer 170 disposed on the electron transport layer 160, and a second electrode 180 disposed on the electron injection layer 170.

In an implementation, the material for an organic electroluminescent device according to an embodiment may be included in at least one of the hole transport layer and the emission layer. In an implementation, the material for an organic electroluminescent device may be included in both layers. In an implementation, the material for an organic electroluminescent device may be included in the hole transport layer 140.

Each of the organic thin layers disposed between the first electrode 120 and the second electrode 180 of the organic electroluminescent device may be formed by various suitable methods, e.g., an evaporation method or the like.

The substrate 110 may be a substrate suitable for use in an organic electroluminescent device. For example, the substrate 110 may be a glass substrate, a semiconductor substrate, or a transparent plastic substrate.

The first electrode 120 may be e.g., an anode and may be formed by an evaporation method, a sputtering method, etc. on the substrate 110. For example, the first electrode 120 may be formed as a transmission type electrode using a metal, an alloy, a conductive compound, etc. having high work function. The first electrode 120 may be formed using e.g., transparent and highly conductive indium tin oxide (ITO), indium zinc oxide (IZO), tin oxide ($SnO_2$), zinc oxide (ZnO), etc. In an implementation, the anode 120 may be formed as a reflection type electrode using magnesium (Mg), aluminum (Al), etc.

On the first electrode 120, the hole injection layer 130 may be formed. The hole injection layer 130 may be a layer equipped with the function of the easy injection of holes from the first electrode 120 and may be formed, e.g., on the first electrode 120 to a thickness of from about 10 nm to about 150 nm. The hole injection layer 130 may be formed using a suitable material. The hole injection layer 130 may include, e.g., triphenylamine-containing poly ether ketone (TPAPEK), 4-isopropyl-4'-methyldiphenyliodoniumtetrakis (pentafluorophenyl)borate (PPBI), N,N'-diphenyl-N,N'-bis-[4-(phenyl-m-tolyl-amino)-phenyl]-phenyl-4,4'-diamine (DNTPD), a phthalocyanine compound such as copper phthalocyanine, 4,4',4"-tris(3-methyl phenylphenylamino) triphenylamine (m-MTDATA), N,N'-di(1-naphthyl)-N,N'-diphenylbenzidine (NPB), 4,4',4"-tris{N,N-diphenylamino}triphenylamine (TDATA), 4,4',4"-tris(N,N-2-naphthylphenylamino)triphenylamine (2-NATA), polyaniline/dodecylbenzenesulfonic acid (Pani/DBSA), poly(3,4-ethylenedioxythiophene)/poly(4-styrenesulfonate) (PEDOT/PSS), polyaniline/camphorsulfonic acid (Pani/CSA), polyaniline/poly(4-styrenesulfonate (PANI/PSS), or the like.

On the hole injection layer 130, the hole transport layer 140 may be formed. The hole transport layer 140 may be formed by stacking a plurality of layers. The hole transport layer 140 may be a layer including a hole transport material equipped with hole transporting function and may be formed, e.g., on the hole injection layer 130 to a thickness from about 10 nm to about 150 nm. The hole transport layer 140 may be formed using the material for an organic electroluminescent device according to an embodiment. In an implementation, in the case in which the material for an organic electroluminescent device according to an embodiment is used as the host material of the emission layer 150, the hole transport layer 140 may be formed using a suitable hole transport material. The hole transport material may include, e.g., 1,1-bis[(di-4-tolylamino)phenyl]cyclohexane (TAPC), a carbazole derivative such as N-phenyl carbazole, polyvinyl carbazole, etc. N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), or the like.

On the hole transport layer 140, the emission layer 150 may be formed. The emission layer 150 may be formed to, e.g., a thickness from about 10 nm to about 60 nm. The material of the emission layer 150 may include a suitable luminescent material, e.g., may be selected from fluoranthene derivatives, pyrene derivatives, arylacetylene derivatives, fluorene derivatives, perylene derivatives, chrysene derivatives, or the like. In an implementation, the pyrene derivatives, the perylene derivatives, and the anthracene derivatives may be used. For example, the material of the emission layer 150 may include, e.g., an anthracene derivative represented by the following Formula 12.

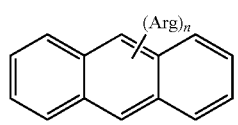

[Formula 12]

In Formula 12, each $Ar_9$ may independently be or include, e.g., a hydrogen atom, a deuterium atom, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted arylthio group having 6 to 50 ring carbon atoms, a substituted or unsubstituted alkoxycarbonyl group having 2 to 50 carbon atoms, a substituted or unsubstituted aryl group having 6 to 50 ring carbon atoms, a heteroaryl group having 5 to 50 ring carbon atoms, a substituted or unsubstituted silyl group, a carboxyl group, a halogen atom, a cyano group, a nitro group, or a hydroxyl group. n may be an integer of 1 to 10.

In an implementation, each $Ar_9$ may include, e.g., a phenyl group, a biphenyl group, a terphenyl group, a naphthyl group, a phenylnaphthyl group, a naphthylphenyl group, a phenanthryl group, a fluorenyl group, an indenyl group, a pyrenyl group, an acetonaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzooxazolyl group, a benzothiazolyl group, a quinoxalyl group, a pyrazolyl group, a dibenzofuranyl group, a dibenzothienyl group, or the like. In an implementation, each $Ar_9$ may include, e.g., the phenyl group, the biphenyl group, the terphenyl group, the fluorenyl group, the carbazolyl group, the dibenzofuranyl group, or the like.

In an implementation, the compound represented by Formula 12 may be one of the following Compounds a-1 to a-12.

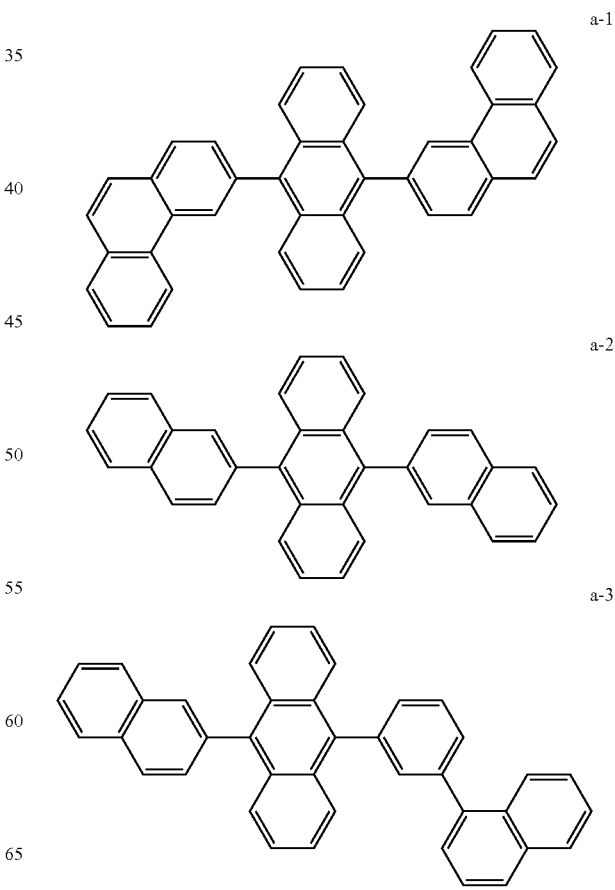

-continued a-4
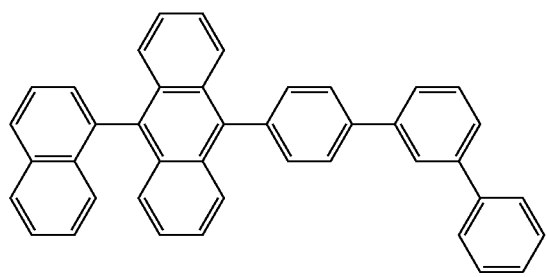

a-5
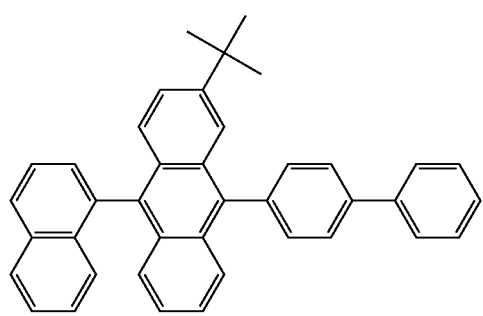

a-6
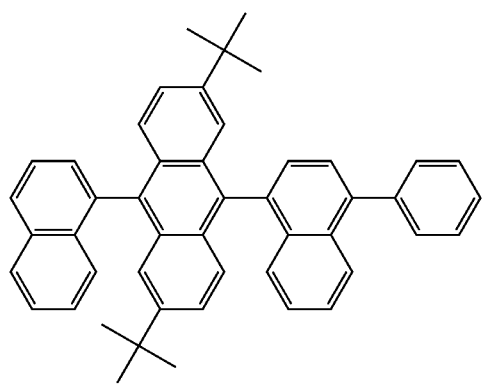

a-7
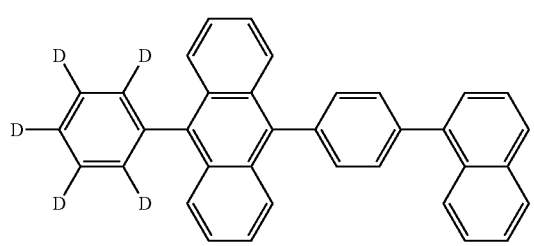

a-8
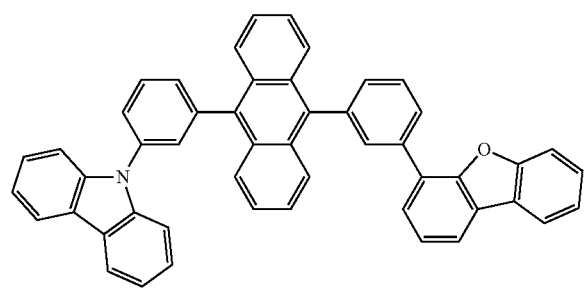

-continued a-9
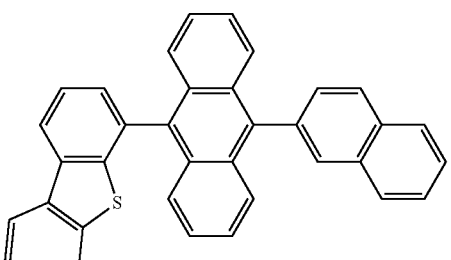

a-10
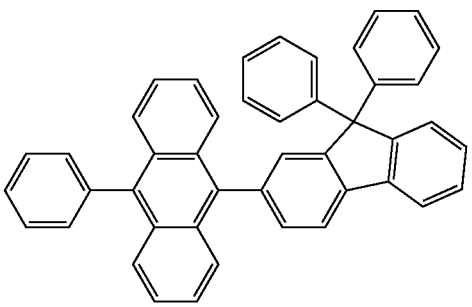

a-11
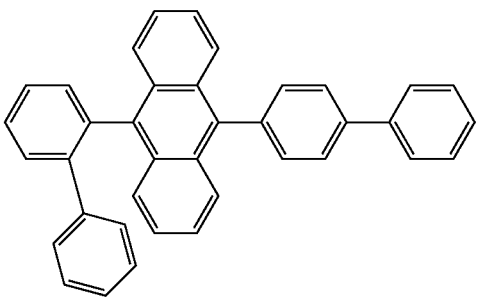

a-12
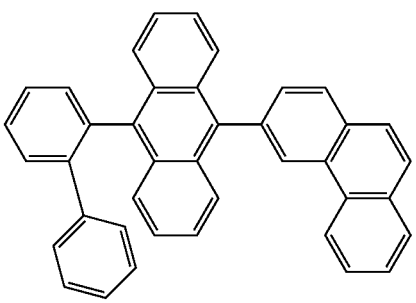

The emission layer 150 may include a dopant such as styryl derivatives (e.g., 1,4-bis[2-(3-N-ethylcarbazolyl)vinyl]benzene (BCzVB), 4-(di-p-tolylamino)-4'-[(di-p-tolylamino)styryl]stilbene (DPAVB), N-(4-((E)-2-(6-((E)-4-(diphenylamino)styryl)naphthalene-2-yl)vinyl)phenyl)-N-phenylbenzeneamine (N-BDAVBi)), perylene and the derivatives thereof (e.g., 2,5,8,11-tetra-t-butylperylene (TBPe)), pyrene and the derivatives thereof (e.g., 1.1-dipyrene, 1,4-dipyrenylbenzene, 1,4-bis(N,N-diphenylamino)pyrene), or the like.

On the emission layer 150, an electron transport layer 160 including a material having tris(8-hydroxyquinolinato)aluminum (Alq$_3$) or a nitrogen-containing aromatic ring (e.g., a material including a pyridine ring such as 1,3,5-tri[(3-pyridyl)-phen-3-yl]benzene, a material including a triazine ring such as 2,4,6-tris(3'-(pyridin-3-yl)biphenyl-3-yl)-1,3,5-triazine, a material including an imidazole derivative such as 2-(4-(N-phenylbenzoimidazolyl-1-ylphenyl)-9,10-dinaphthylanthracene) may be formed. The electron transport layer 160 may be a layer including an electron transport material for an electron transport function and may be formed on the emission layer 150 to a thickness from about 15 nm to about 50 nm. On the electron transport layer 160, the electron injection layer 170 may be formed using a material including e.g., lithium fluoride, lithium-8-quinolinato (Liq), or the like. The electron injection layer 170 may be a layer for facilitating injection of electrons from the second electrode 180 and may be formed to a thickness from about 0.3 nm to about 9 nm.

In addition, on the electron injection layer 170, the second electrode 180 may be formed. The second electrode 180 may be, e.g., a cathode. For example, the second electrode 180 may be formed as a reflection type electrode using a metal, an alloy, a conductive compound, etc. having low work function. The second electrode 180 may be formed using e.g., lithium (Li), magnesium (Mg), aluminum (Al), aluminum-lithium (Al—Li), calcium (Ca), magnesium-indium (Mg—In), magnesium-silver (Mf—Ag), etc. In addition, the second electrode 180 may be formed as a transmission type electrode using ITO, IZO, etc. Each of the above-mentioned layers may be formed by selecting an appropriate layer forming method such as a vacuum evaporation method, a sputtering method, various coating methods, etc. according to materials used.

The organic electroluminescent device 100 including the material for an organic electroluminescent device according to an embodiment may have improved emission life.

In an implementation, the organic electroluminescent device 100 according to embodiments may be formed using the structures of various other suitable organic electroluminescent devices. For example, the organic electroluminescent device 100 may not be provided with one or more layers of the hole injection layer 130, the electron transport layer 160, and the electron injection layer 170. In an implementation, each layer of the organic electroluminescent device 100 may be formed as a single layer or a multilayer.

In an implementation, the organic electroluminescent device 100 may be provided with a hole blocking layer between the electron transport layer 160 and the emission layer 150 to help prevent the diffusion of triplet excitons or holes to the electron transport layer 160. In an implementation, the hole blocking layer may be formed using e.g., oxadiazole derivatives, triazole derivatives or phenanthroline derivatives.

EXAMPLES

Hereinafter, the organic electroluminescent device according to an embodiment of the present disclosure will be explained in particular referring to examples and comparative examples. However, The following Examples and Comparative Examples are only illustrations of the present disclosure, and the scope of the present disclosure is not limited thereto.

Synthetic Example 1: Synthesis of Compound C

Compound C was synthesized according to the following synthetic scheme.

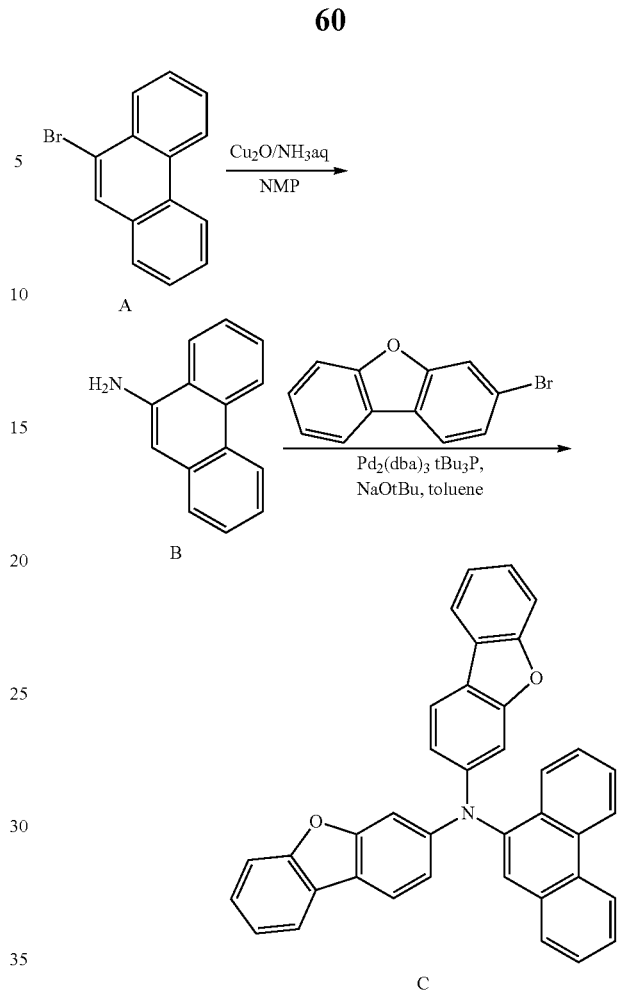

(Synthesis of Compound B)

Under an argon atmosphere, 15.00 g of Compound A, 0.85 g of cuprous oxide, 20 ml of an aqueous ammonia solution, and 70 ml of NMP were added to a 500 ml three necked flask, followed by heating at about 110° C. for about 25 hours. After air cooling, water was added, an organic layer was separated, and solvents were distilled. The crude product thus obtained was separated using silica gel column chromatography (hexane/ethyl acetate) to produce 7.4 g of Compound B as a white solid (Yield 66%). The molecular weight of Compound B thus obtained was measured using FAB-MS, and a value of 193 ($C_{14}H_{11}N$) was obtained.

(Synthesis of Compound C)

Figure 2:
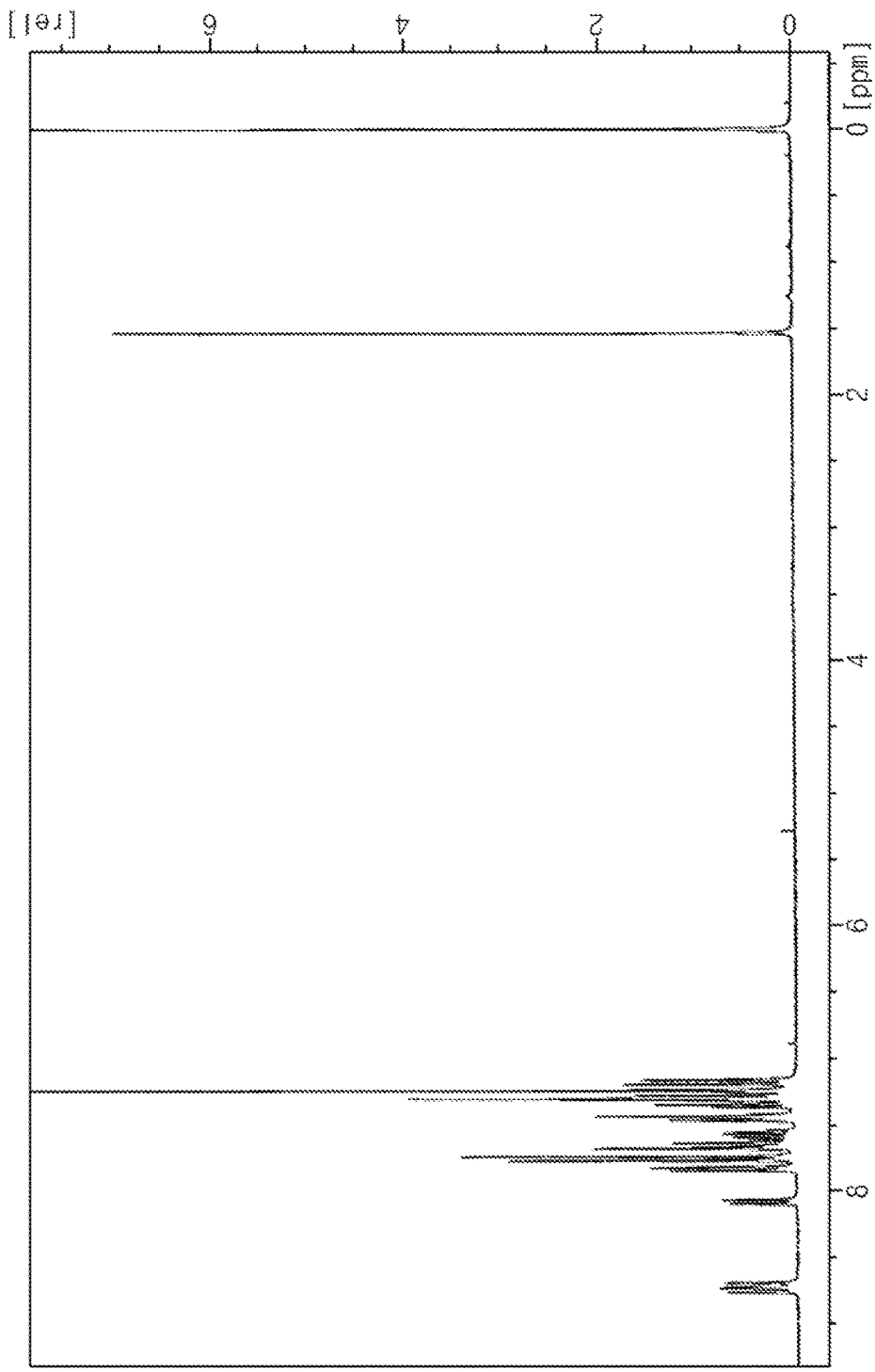
FIG. 2 illustrates an NMR spectrum of Compound C according to an embodiment.

Under an argon atmosphere, 1.00 g of Compound B, 2.81 g of 3-bromo-dibenzofuran, 0.27 g of bis(dibenzylideneacetone)palladium(0), 0.088 g of tri-tert-butylphosphine and 3.98 g of sodium tert-butoxide were added to a 500 ml three necked flask, followed by heating and refluxing in 200 ml of a toluene solvent for about 7 hours. After air cooling, water was added to the reactant, an organic layer was separated, and solvents were distilled. The crude product thus obtained was separated using silica gel column chromatography (toluene/hexane) to produce 1.90 g of Compound C as a white solid (Yield 70%). The molecular weight of Compound C thus obtained was measured using FAB-MS, and a value of 525 ($C_{38}H_{23}NO_2$) was obtained. In addition, $^1$H NMR (CDCl$_3$, 300 MHz) of Compound C was measured, and the chemical shift values shown in FIG. 2 were obtained. Thus, the synthesis of Compound C was secured. In addition, the glass transition temperature of Compound C was measured using a differential scanning calorimetry, DSC 7020 of Hitachi Hightech Co., and a value of Tg: 120° C. was obtained.

Synthetic Example 2: Synthesis of Compound E

Compound E was synthesized according to the following synthetic scheme.

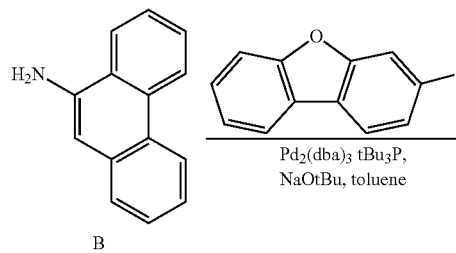

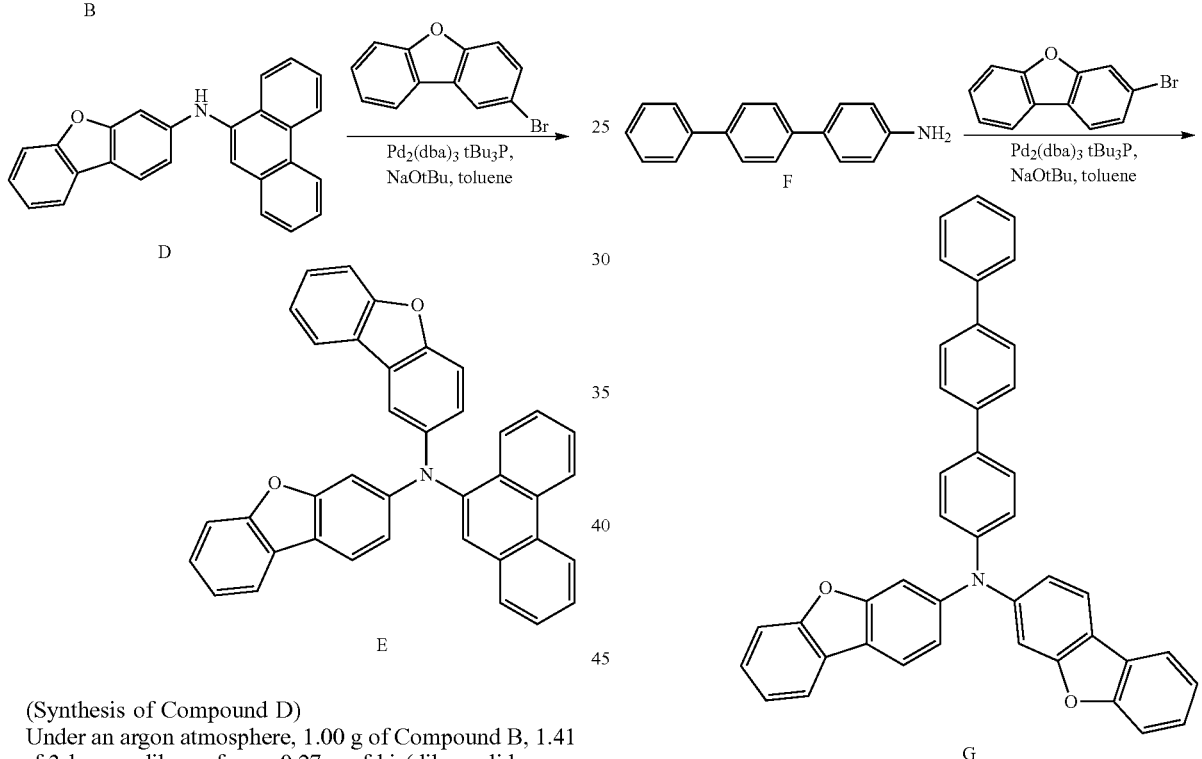

(Synthesis of Compound D)

Under an argon atmosphere, 1.00 g of Compound B, 1.41 g of 3-bromo-dibenzofuran, 0.27 g of bis(dibenzylideneacetone)palladium(0), 0.088 g of tri-tert-butylphosphine and 3.98 g of sodium tert-butoxide were added to a 500 ml three necked flask, followed by heating and refluxing in 200 ml of a toluene solvent for about 7 hours. After air cooling, water was added to the reactant, an organic layer was separated, and solvents were distilled. The crude product thus obtained was separated using silica gel column chromatography (toluene and hexane) to produce 1.10 g of Compound D as a white solid (Yield 59%). The molecular weight of Compound D thus obtained was measured using FAB-MS, and a value of 359 ($C_{26}H_{17}NO$) was obtained.

(Synthesis of Compound E)

Under an argon atmosphere, 1.00 g of Compound D, 0.75 g of 3-bromo-dibenzofuran, 0.13 g of bis(dibenzylideneacetone)palladium(0), 0.044 g of tri-tert-butylphosphine and 1.99 g of sodium tert-butoxide were added to a 500 ml three necked flask, followed by heating and refluxing in 200 ml of a toluene solvent for about 7 hours. After air cooling, water was added to the reactant, an organic layer was separated, and solvents were distilled. The crude product thus obtained was separated using silica gel column chromatography (toluene and hexane) to produce 1.10 g of Compound E as a white solid (Yield 75%). The molecular weight of Compound E thus obtained was measured using FAB-MS, and a value of 525 ($C_{38}H_{23}NO_2$) was obtained. In addition, $^1$H NMR (CDCl$_3$, 300 MHz) of Compound E was measured, and the chemical shift values expected from the structure of Compound E were obtained. Thus, the synthesis of Compound E was secured. In addition, the glass transition temperature of Compound E was measured using a differential scanning calorimetry, DSC 7020 of Hitachi Hightech Co., and a value of Tg: 115° C. was obtained.

Synthetic Example 3: Synthesis of Compound G

Compound G was synthesized according to the following synthetic scheme.

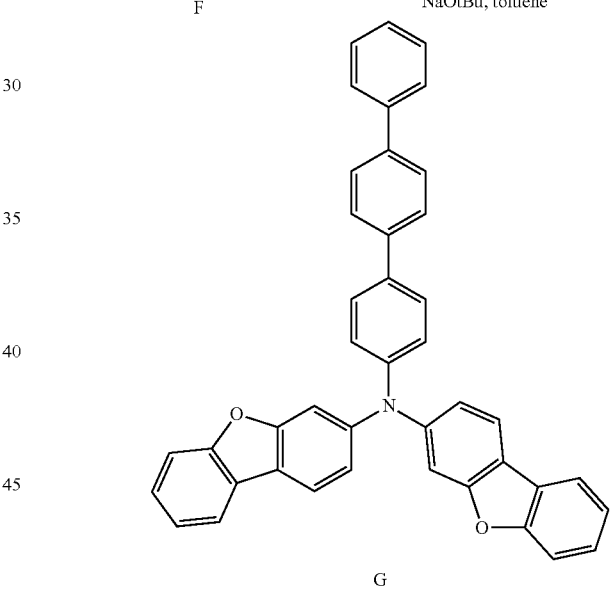

Under an argon atmosphere, 1.34 g of Compound F, 2.96 g of 3-bromo-dibenzofuran, 0.27 g of bis(dibenzylideneacetone)palladium(0), 0.088 g of tri-tert-butylphosphine and 3.98 g of sodium tert-butoxide were added to a 500 ml three necked flask, followed by heating and refluxing in 200 ml of a toluene solvent for about 7 hours. After air cooling, water was added to the reactant, an organic layer was separated, and solvents were distilled. The crude product thus obtained was separated using silica gel column chromatography (toluene and hexane) to produce 2.20 g of Compound G as a white solid (Yield 70%). The molecular weight of Compound G thus obtained was measured using FAB-MS, and a value of 577 ($C_{42}H_{27}NO_2$) was obtained. In addition, $^1$H NMR (CDCl$_3$, 300 MHz) of Compound G was measured, and the chemical shift values expected from the structure of Compound G were obtained. Thus, the synthesis of Compound G was secured. In addition, the glass transition temperature of Compound G was measured using a differential scanning calorimetry, DSC 7020 of Hitachi Hightech Co., and a value of Tg: 100° C. was obtained.

Synthetic Example 4: Synthesis of Compound I

Compound I was synthesized according to the following synthetic scheme.

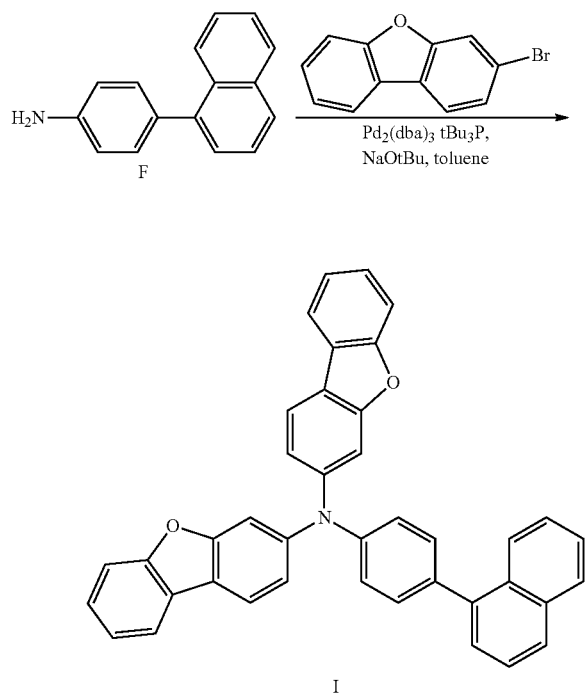

Under an argon atmosphere, 1.13 g of Compound H, 2.81 g of 3-bromo-dibenzofuran, 0.27 g of bis(dibenzylideneacetone)palladium(0), 0.088 g of tri-tert-butylphosphine and 3.98 g of sodium tert-butoxide were added to a 500 ml three necked flask, followed by heating and refluxing in 200 ml of a toluene solvent for about 7 hours. After air cooling, water was added to the reactant, an organic layer was separated, and solvents were distilled. The crude product thus obtained was separated using silica gel column chromatography (toluene/hexane) to produce 1.85 g of Compound I as a white solid (Yield 65%). The molecular weight of Compound I thus obtained was measured using FAB-MS, and a value of 551 ($C_{40}H_{25}NO_2$) was obtained. In addition, $^1$H NMR (CDCl$_3$, 300 MHz) of Compound I was measured, and the chemical shift values expected from the structure of Compound I were obtained. Thus, the synthesis of Compound I was secured. In addition, the glass transition temperature of Compound I was measured using a differential scanning calorimetry, DSC 7020 of Hitachi Hightech Co., and a value of Tg: 100° C. was obtained.

(Manufacture of Organic Electroluminescent Device)

An organic electroluminescent device was manufactured by the following method. First, on an ITO-glass substrate patterned and washed in advance, surface treatment using UV-ozone (O$_3$) was conducted. The layer thickness of an ITO layer (the first electrode) was about 150 nm. After ozone treatment, the substrate was washed. After finishing washing, the substrate was set in a glass bell jar type evaporator for forming an organic layer, and a hole injection layer, a HTL (a hole transport layer), an emission layer and an electron transport layer were evaporated one by one in a vacuum degree of about $10^{-4}$ to about $10^{-5}$ Pa. The material of the hole injection layer was 2-TNATA, and the thickness thereof was about 60 nm. The materials of the HTL are shown in Table 1, below, and the thickness thereof was about 30 nm.

In addition, the thickness of the emission layer was about 25 nm. The host of the emission material was 9,10-di(2-naphthyl)anthracene (ADN). A dopant was 2,5,8,11-tetra-t-butylperylene (TBP). The doped amount of the dopant was about 3 wt % on the basis of the weight of the host. The material of the electron transport layer was Alq$_3$, and the thickness thereof was about 25 nm. Subsequently, the substrate was transferred to a glass bell jar type evaporator for forming a metal layer, and the electron injection layer and a cathode material were evaporated in a vacuum degree of about $10^{-4}$ to about $10^{-5}$ Pa. The material of the electron injection layer was LiF, and the thickness thereof was about 1.0 nm. The material of the second electrode was Al, and the thickness thereof was about 100 nm.

TABLE 1

| Example of device manufacture | HTL | Current density (mA/cm$^2$) | Voltage (V) | Life LT50 (hr) |
|---|---|---|---|---|
| Example 1 | Compound C | 10 | 6.3 | 2,000 |
| Example 2 | Compound E | 10 | 6.5 | 1,800 |
| Example 3 | Compound G | 10 | 6.6 | 2,200 |
| Example 4 | Compound I | 10 | 6.6 | 2,100 |
| Comparative Example 1 | Comparative Compound C1 | 10 | 6.6 | 1,100 |
| Comparative Example 2 | Comparative Compound C2 | 10 | 8.2 | 1,300 |
| Comparative Example 3 | Comparative Compound C3 | 10 | 7.6 | 1,300 |

In Table 1, Comparative Compounds C1, C2, and C3 are illustrated below.

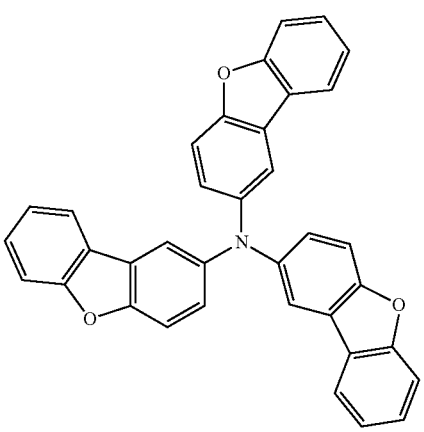

-continued

C2

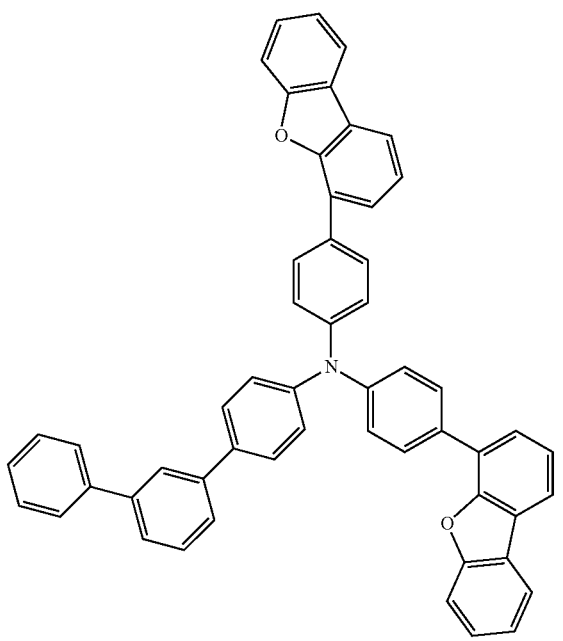

C3

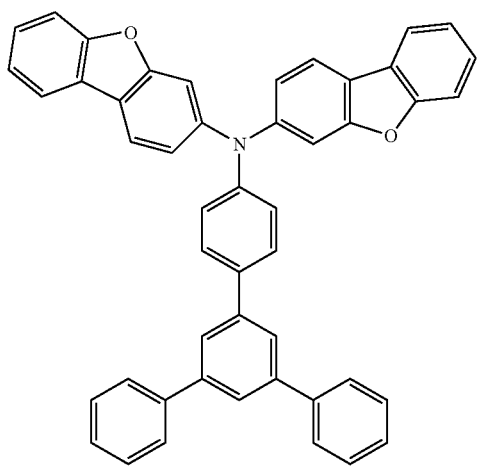

(Evaluation of Properties)

Then, the driving voltage and the emission life of the organic electroluminescent devices were measured. In addition, the electroluminescent properties of the organic EL device 100 thus manufactured were evaluated using C9920-11 brightness light distribution characteristics measurement system of HAMAMATSU Photonics Co. In addition, current density was measured at 10 mA/cm², and half-life was measured at 1,000 cd/m². The results are shown in Table 1.

According to Table 1, the life was improved for Examples 1 to 4 when compared to that of Comparative Examples 1 to 3. Particularly, the life was more improved for Examples 1, 3 and 4 when compared to that of Comparative Example 3. It would be found that a structure including an aryl group in which three phenyl groups were combined and condensed exhibited improved effects of the life. When comparing Examples 1 and 2, all properties of Example 1 were better than those of Example 2. In addition, When comparing Example 3 and Comparative Example 1, the emission life of Example 3 was improved greatly than Comparative Example 1. Thus, it would be preferable that all dibenzo-furanyl groups were combined with a nitrogen atom at position 3. In exemplary embodiments, the emission life of the organic electroluminescent device was largely improved specifically in a blue region. In addition, since a compound group according to exemplary embodiments has a wide energy gap which may correspond to a blue region, application from a green region to a red region may be possible.

By way of summation and review, in an organic electroluminescent device, holes and electrons injected from the anode and the cathode may recombine in the emission layer to generate excitons, and light may be emitted via the transition of the excitons to a ground state. As a hole transport material used in the hole transport layer, e.g., a monoamine compound including a dibenzofuranyl group may be used.

An organic electroluminescent device including some monoamine compounds as a hole transport material may not provide satisfactory values concerning emission life. For example, a monoamine compound derivative may not provide satisfactory values of the emission life of the organic electroluminescent device.

The embodiments may provide a material for an organic electroluminescent device which may help improve the emission life of an organic electroluminescent device.

According to an embodiment, the emission life of the organic electroluminescent device may be improved.

As described above, the material for an organic electroluminescent device according to an embodiment may have the configuration of Formula 1, and the emission life of the organic electroluminescent device using the same may be largely improved. Thus, the material for an organic electroluminescent device according to exemplary embodiments may be practically used in various areas.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A material for an organic electroluminescent device, the material comprising a monoamine compound represented by the following Formula 1:

[Formula 1]

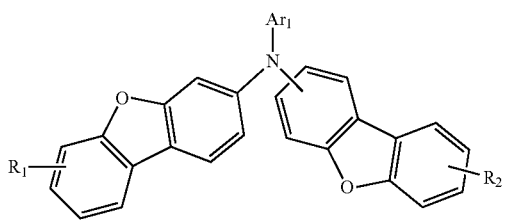

wherein, in Formula 1, $R_1$ and $R_2$ are each independently a hydrogen atom, a halogen atom, an alkyl group having 1 to 15 carbon atoms, a substituted or unsubstituted aryl group having 6 to 30 ring carbon atoms, or a substituted or unsubstituted heteroaryl group having 1 to 30 ring carbon atoms, and Ar$_1$ is a substituted or unsubstituted phenanthrenyl group.

2. The material for an organic electroluminescent device as claimed in claim 1, wherein all dibenzofuranyl groups that are directly bonded with a nitrogen atom of the monoamine are bound to the nitrogen atom at a 3 position of the dibenzofuranyl group.

3. A material for an organic electroluminescent device, wherein the material includes one of the following compounds:

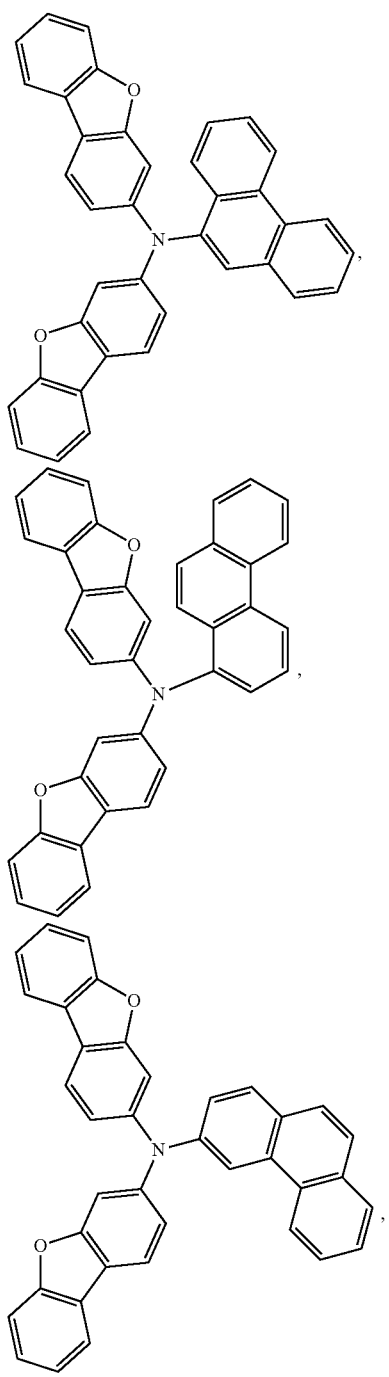

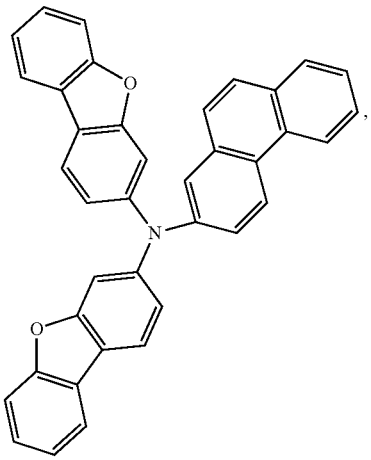

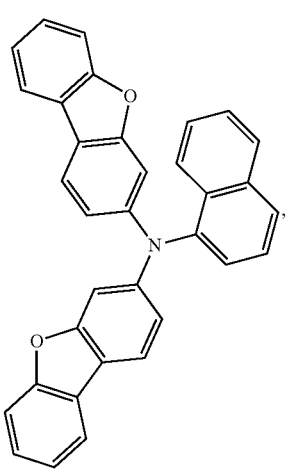

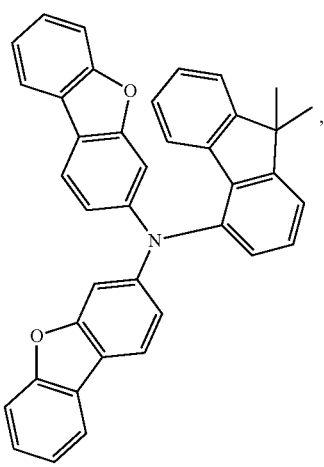

69
-continued
70
-continued
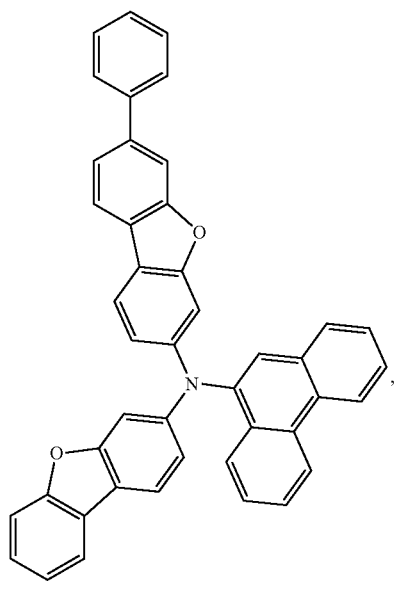
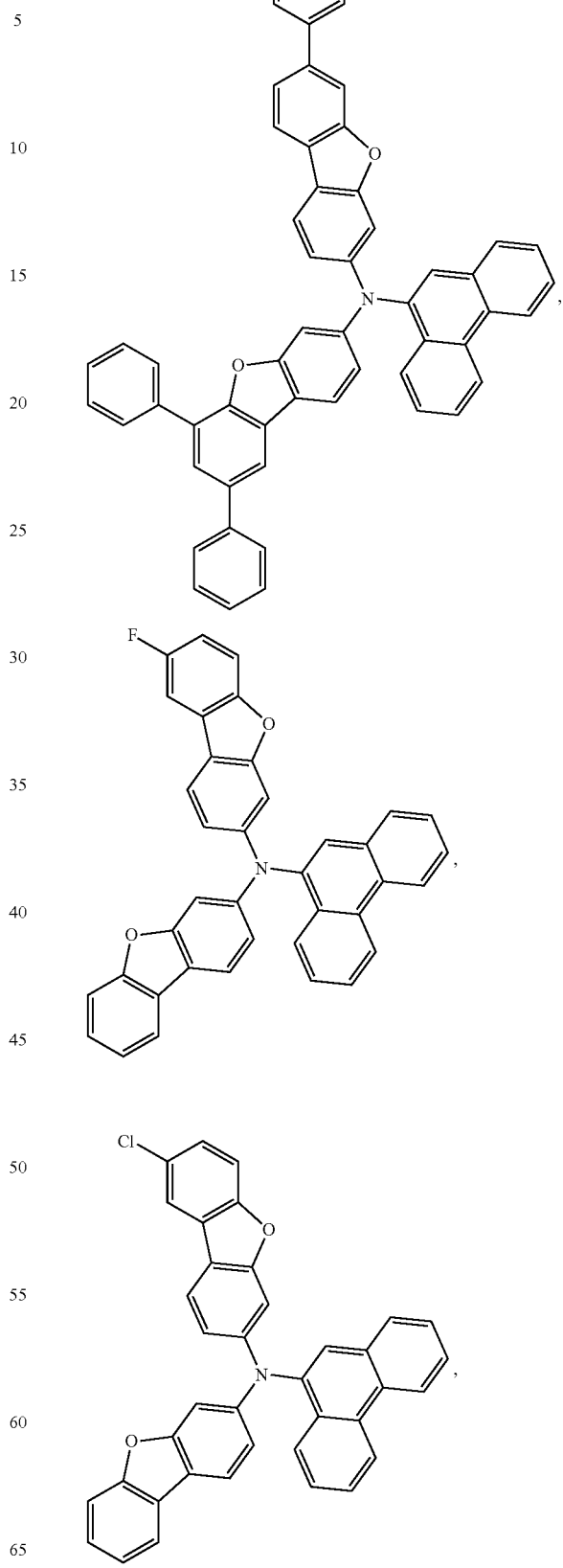

71
-continued
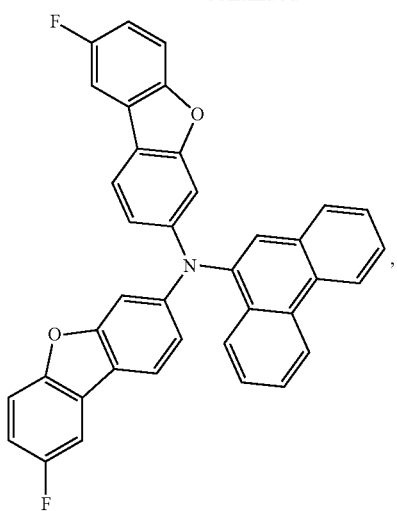
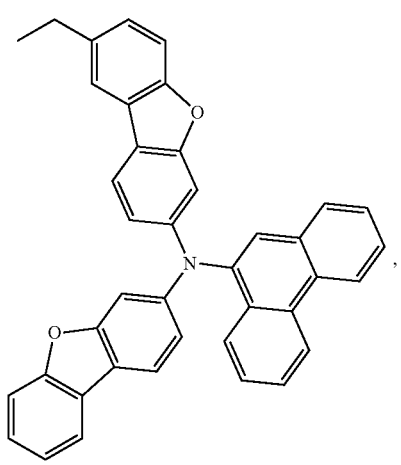
72
-continued
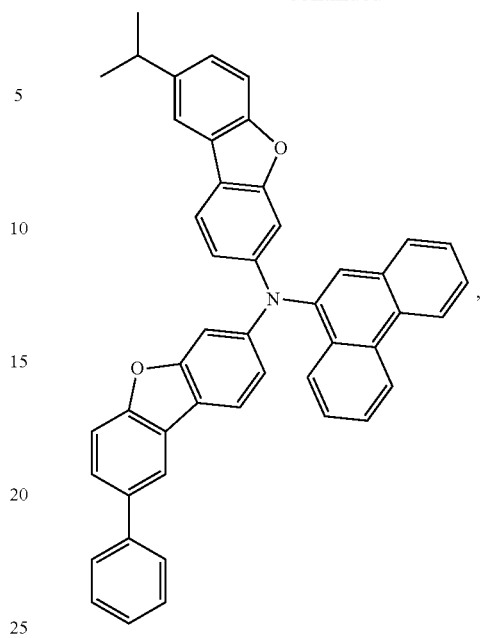
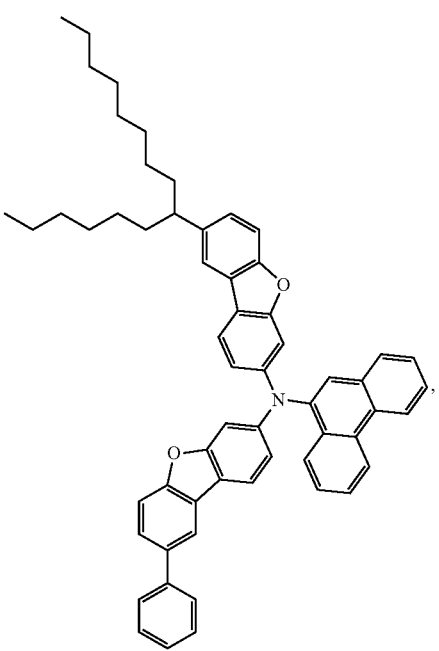

73
-continued
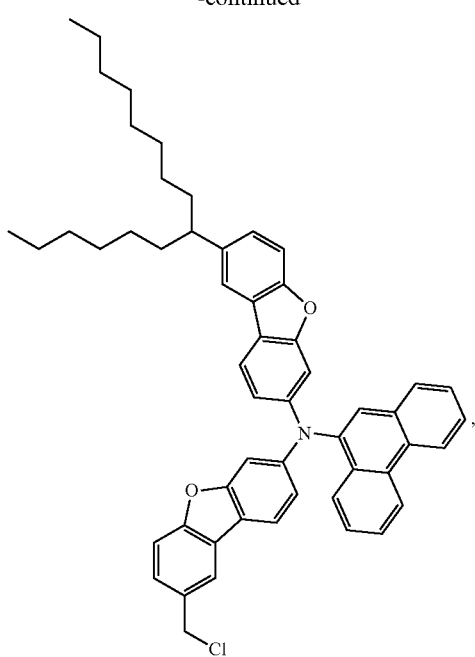
74
-continued
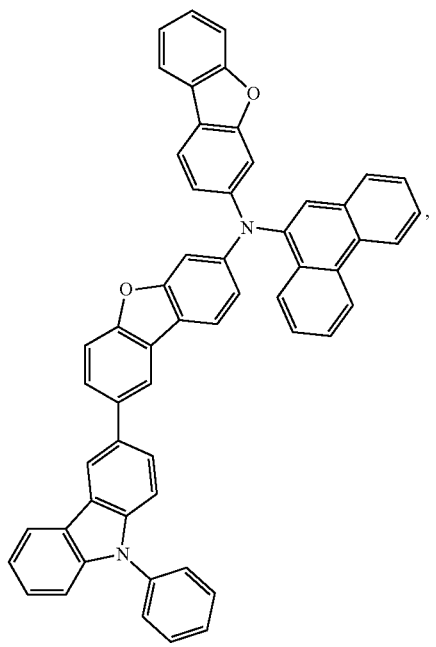
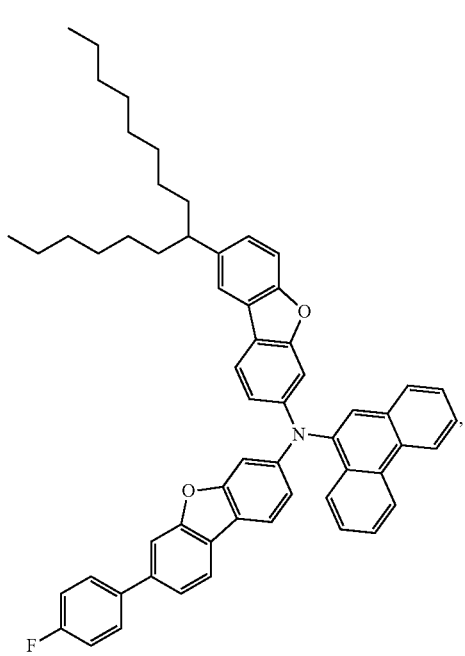

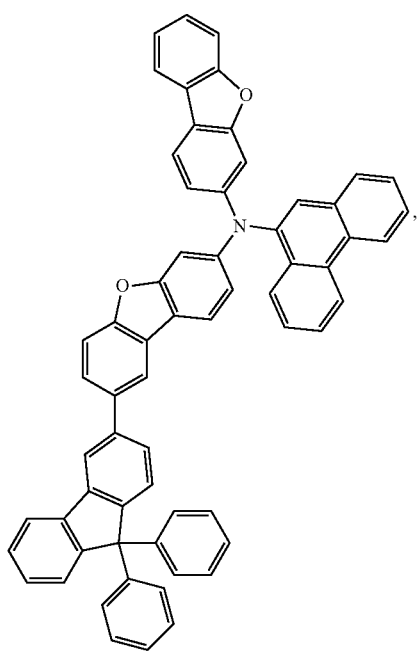
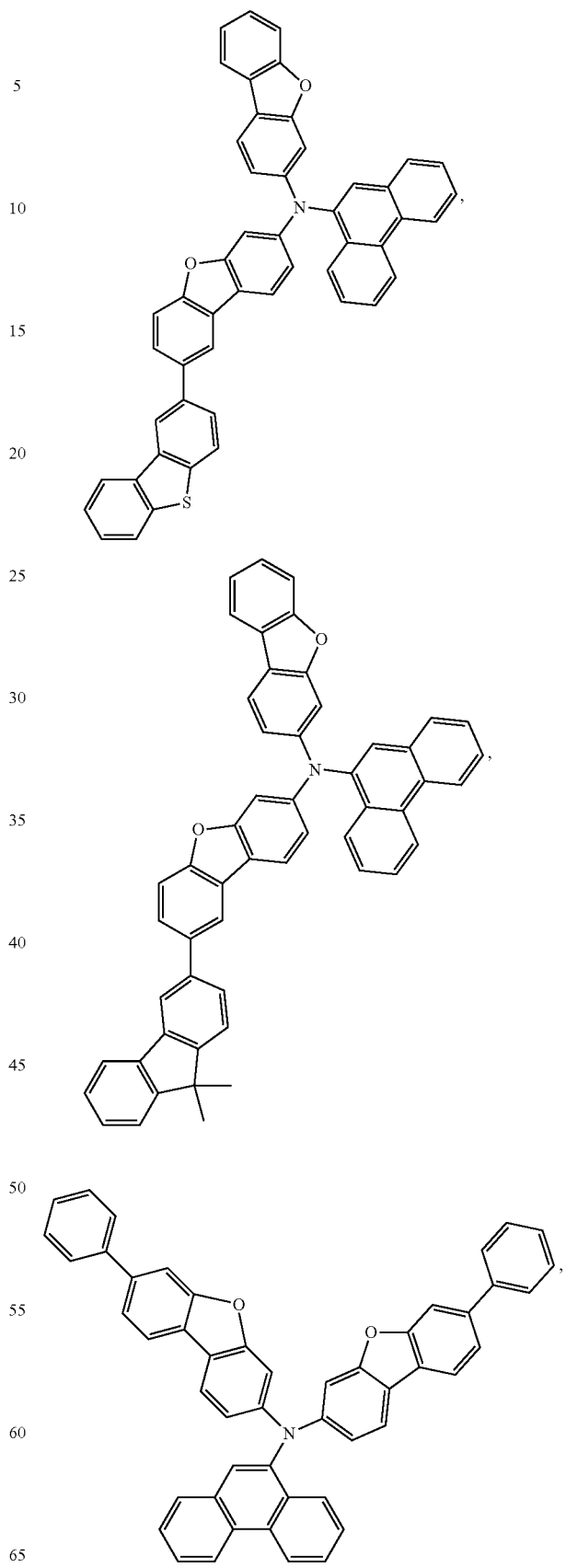

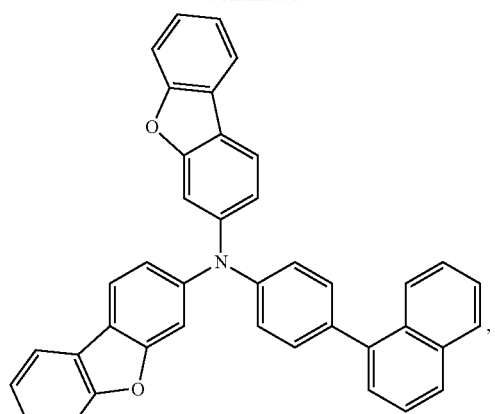
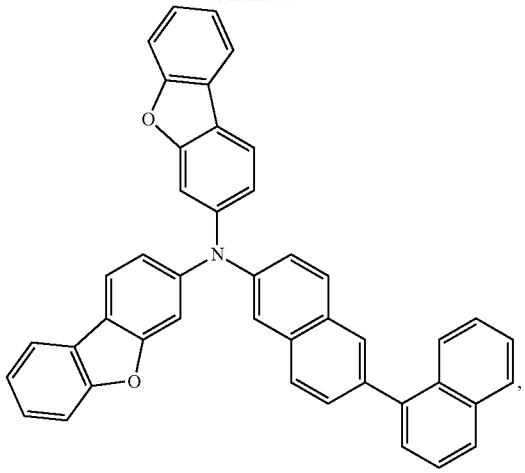
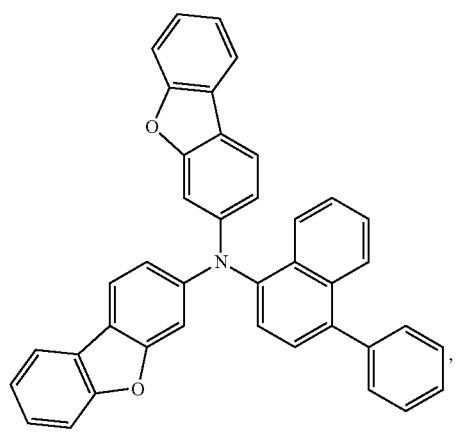
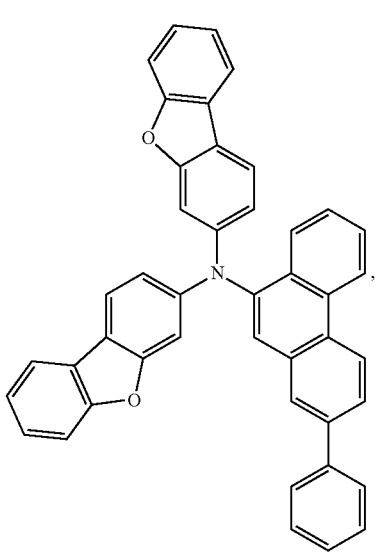
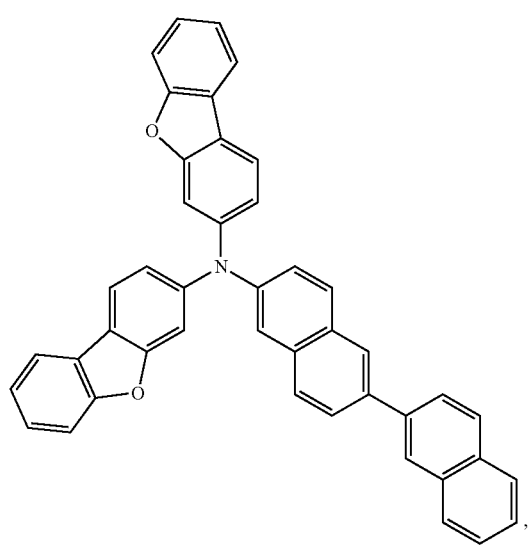
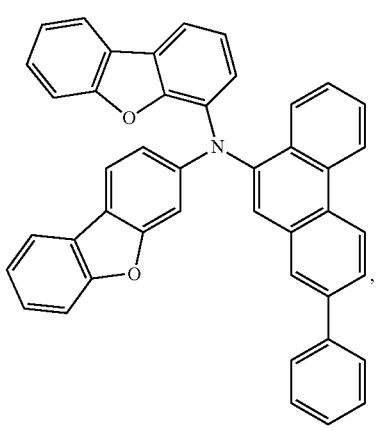

79
-continued
80
-continued
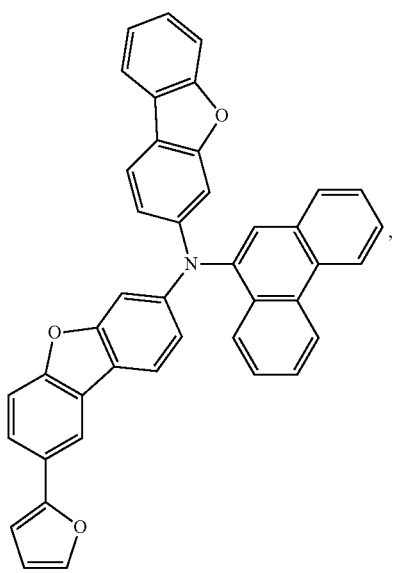
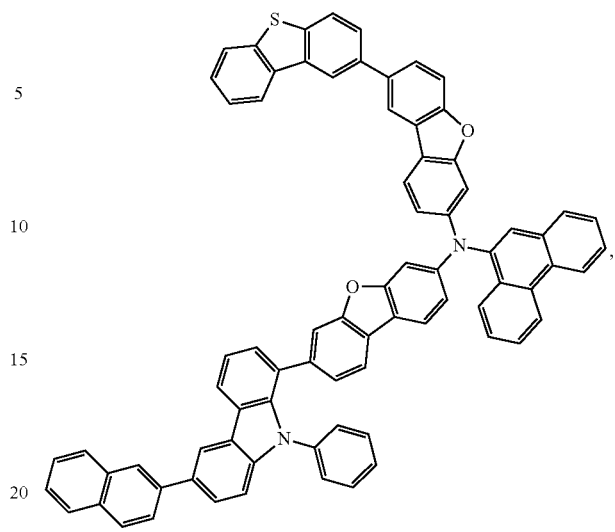
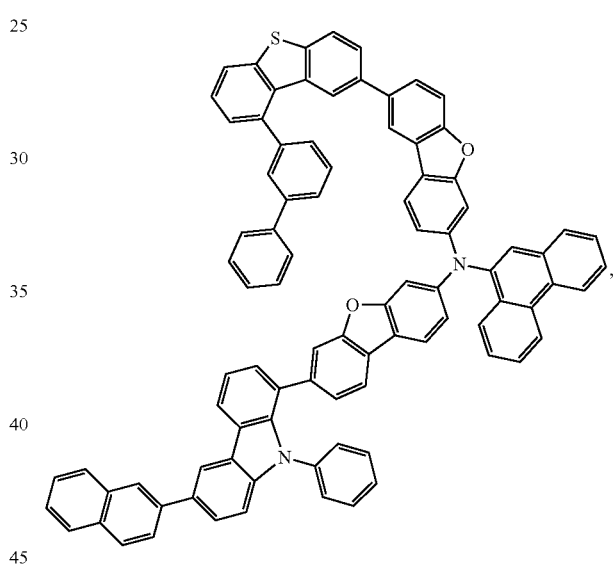
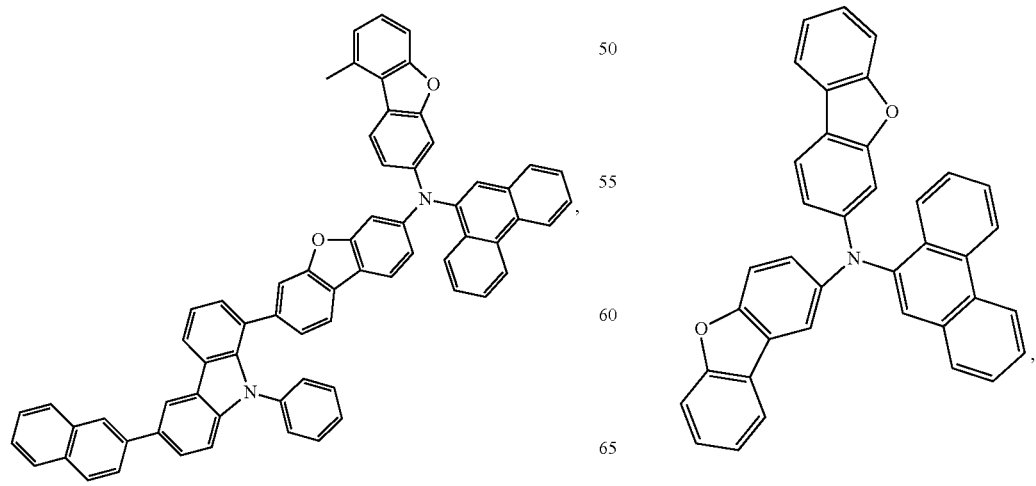

81
-continued
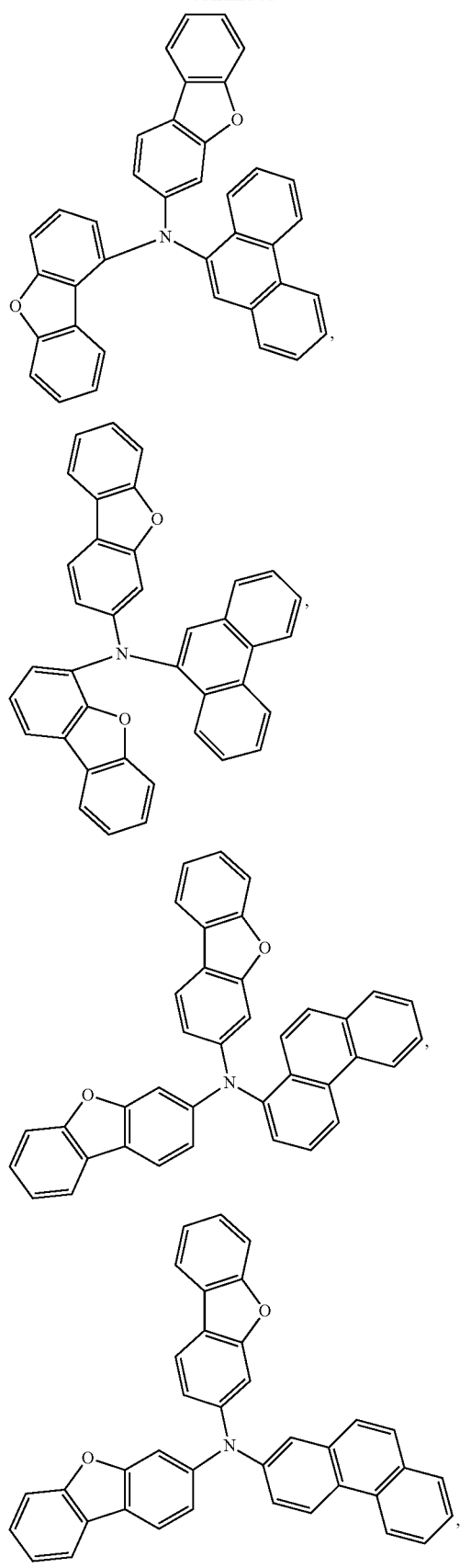
82
-continued
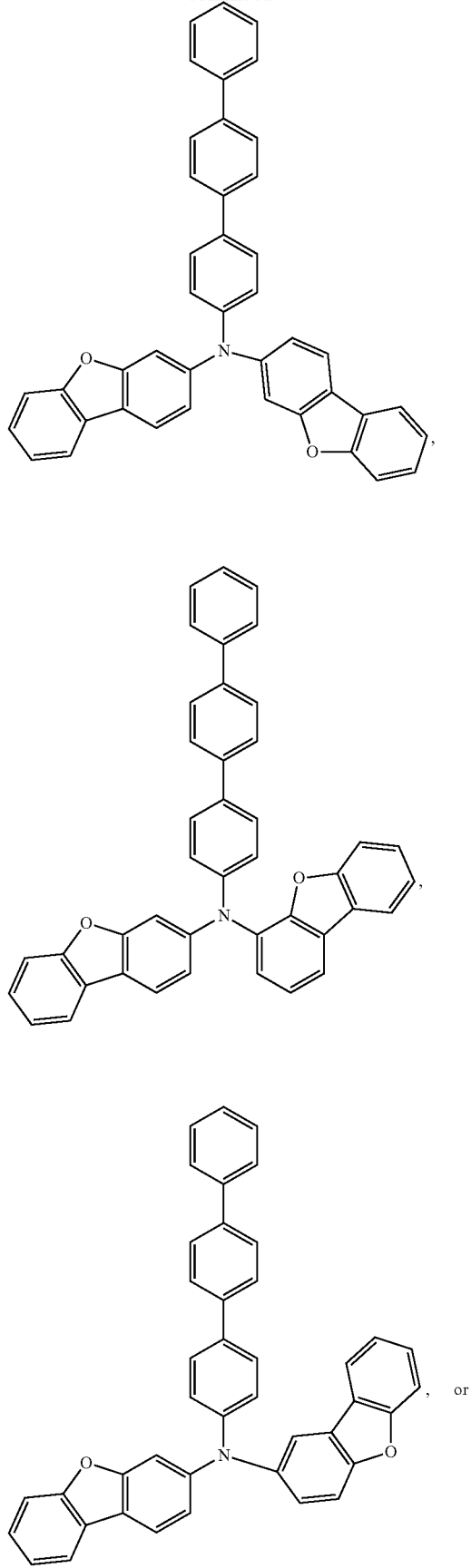

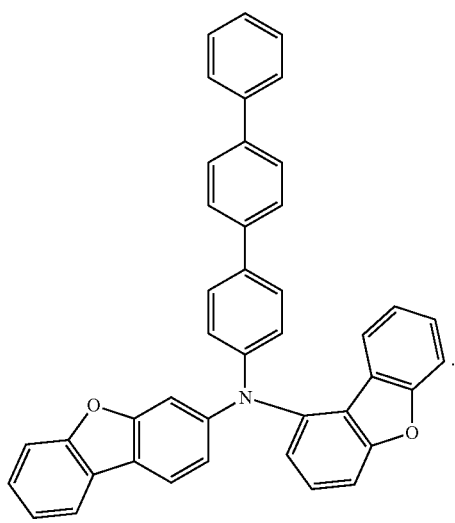

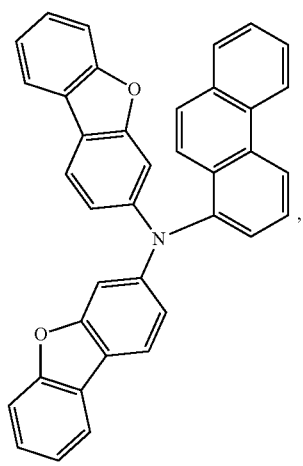

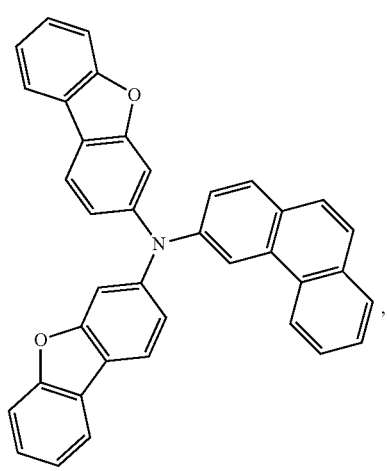

4. An organic electroluminescent device comprising the material for an organic electroluminescent device as claimed in claim 1.

5. The organic electroluminescent device as claimed in claim 4, wherein the material for an organic electroluminescent device is included in a hole transport layer.

6. An organic electroluminescent device comprising a material for an organic electroluminescent device, wherein the material includes one of the following compounds:

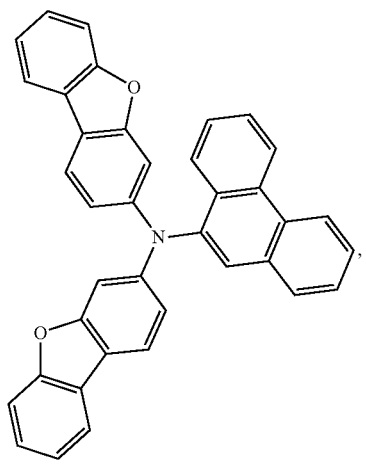

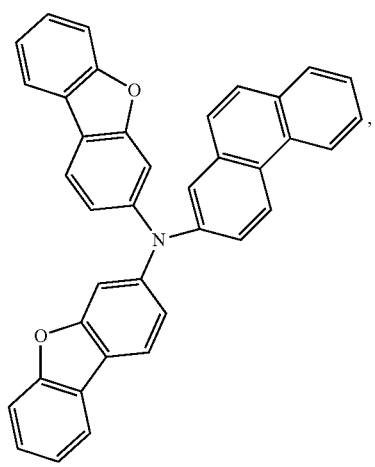

85
-continued
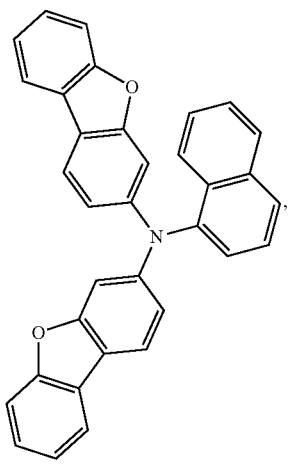
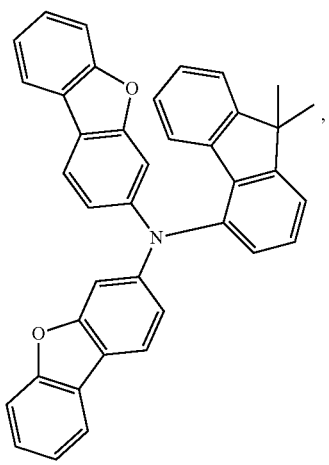
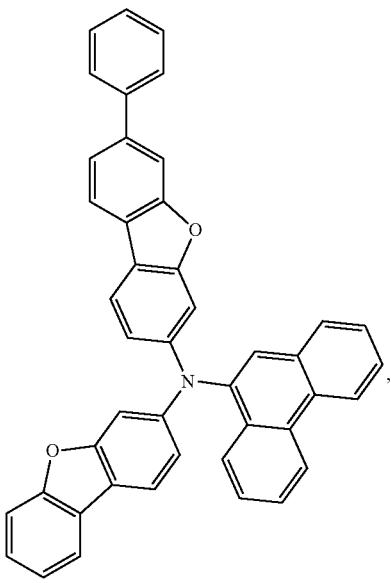
86
-continued
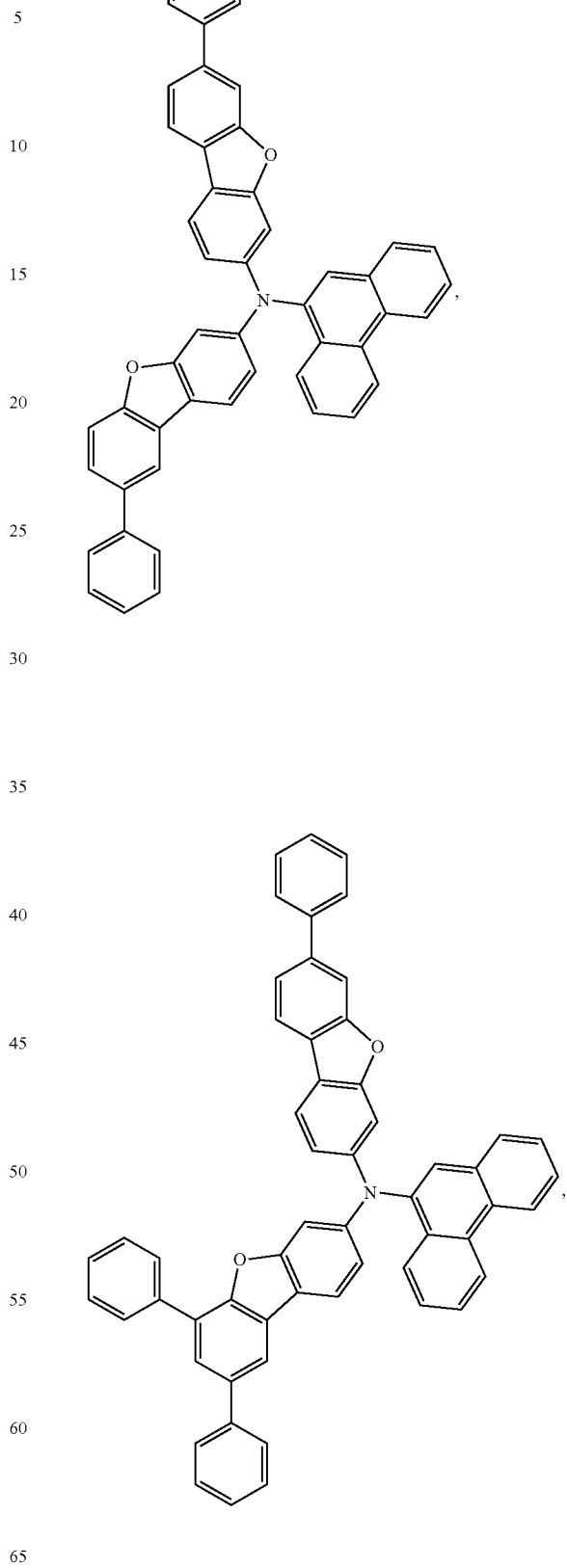

87
-continued
88
-continued
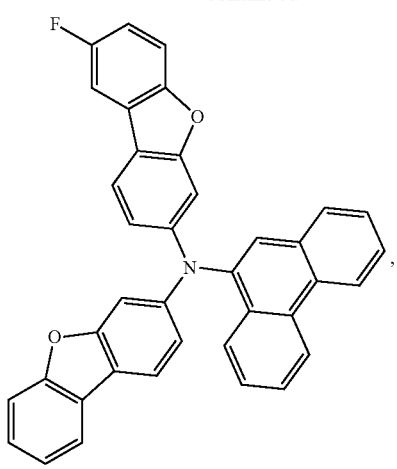
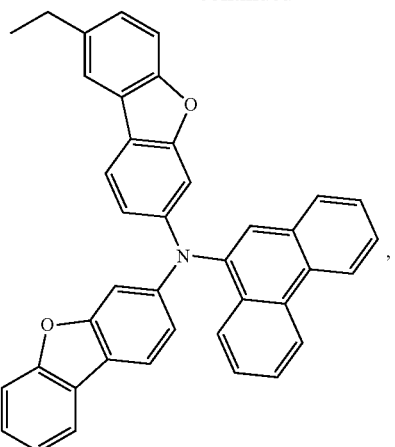

89
-continued
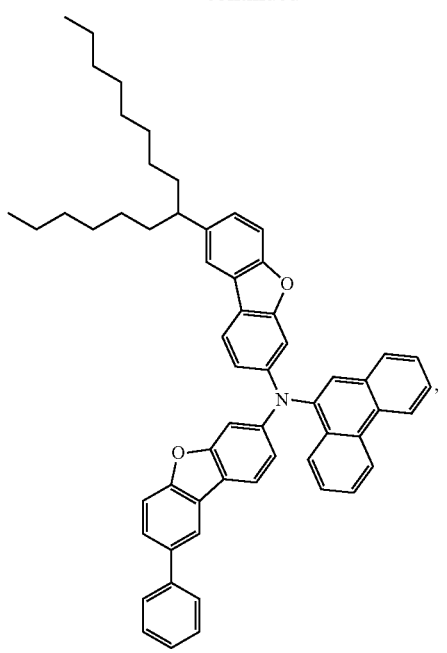
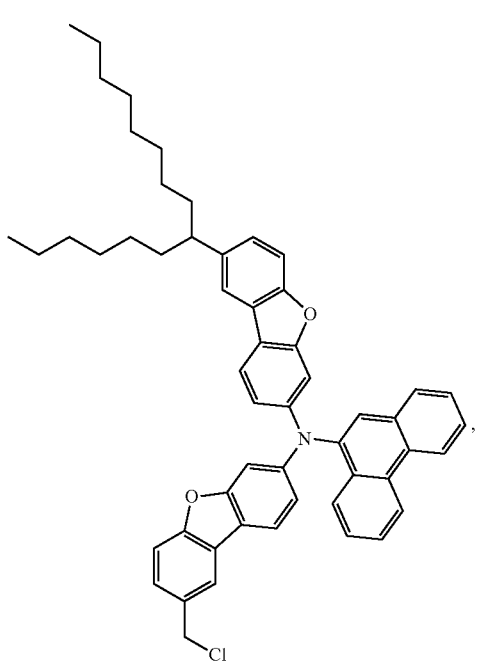
90
-continued
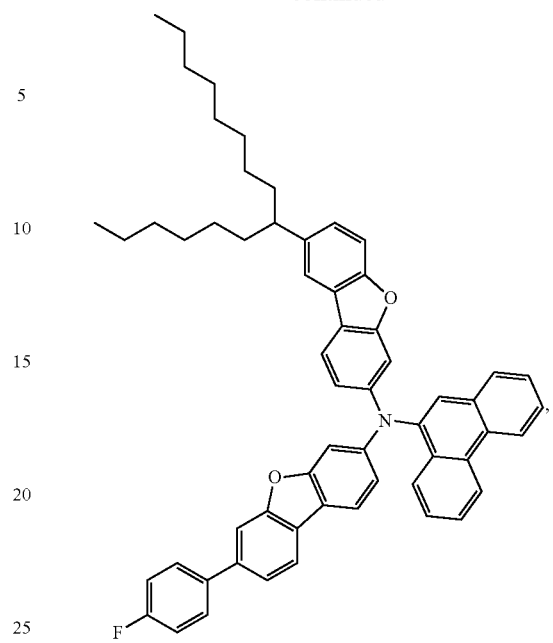
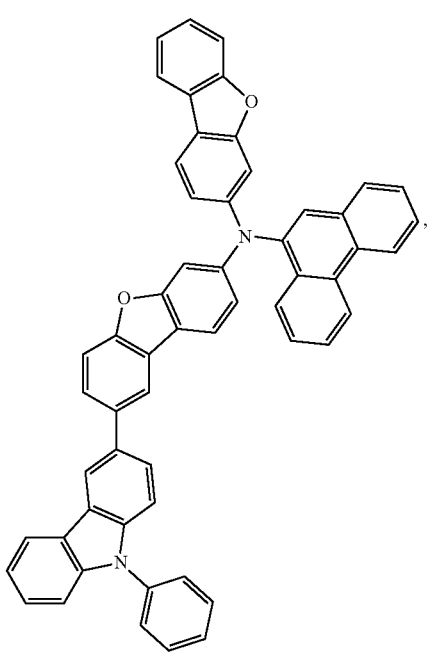

91
-continued
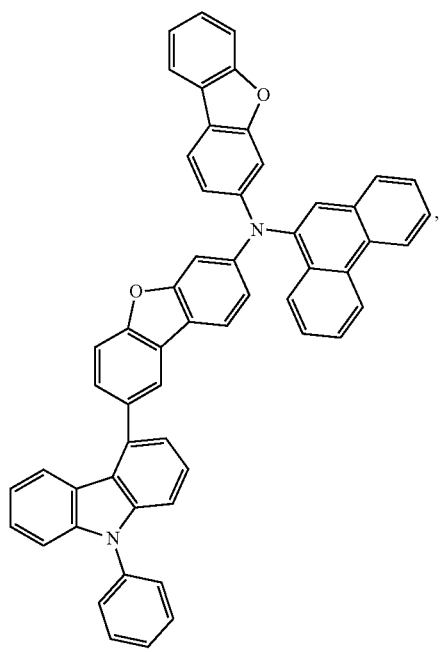
92
-continued
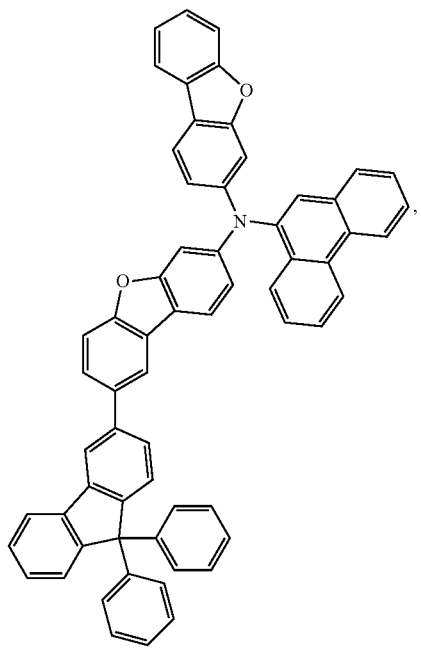
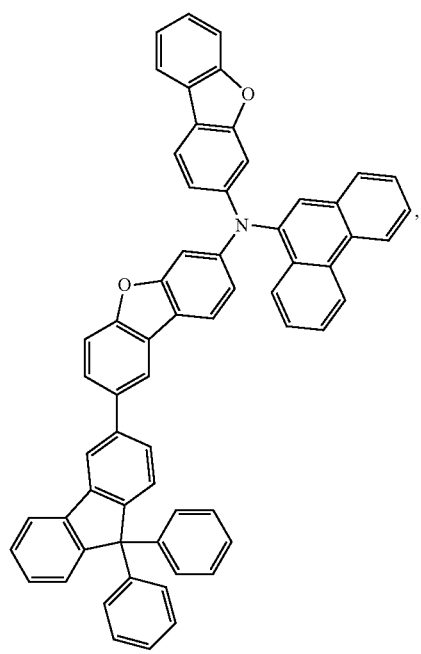
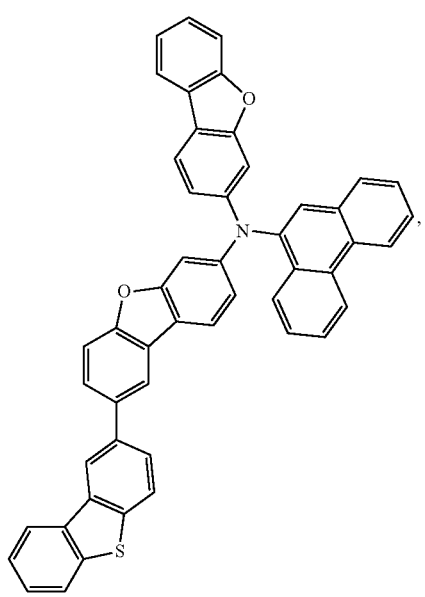

93
-continued
94
-continued
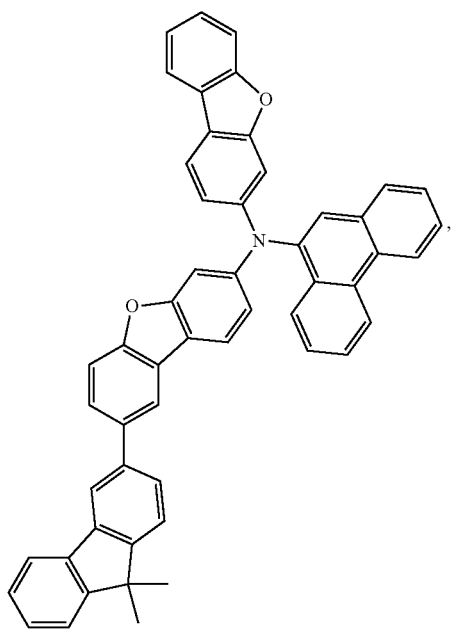
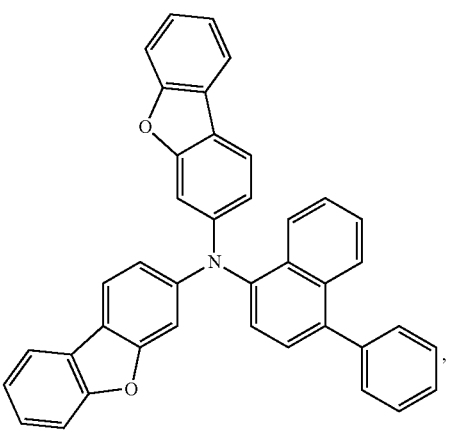
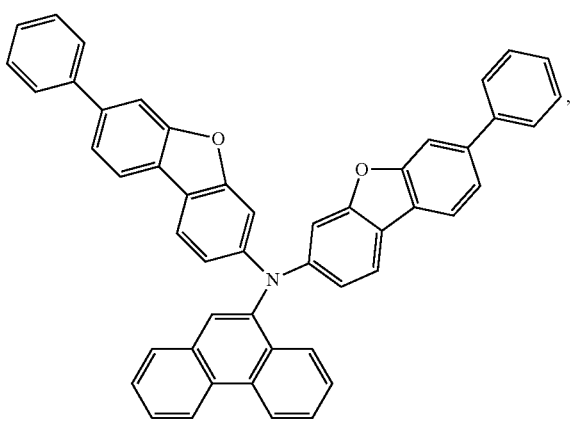
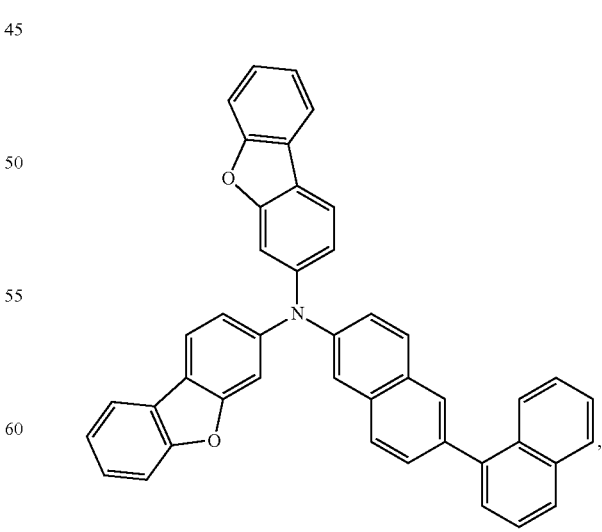

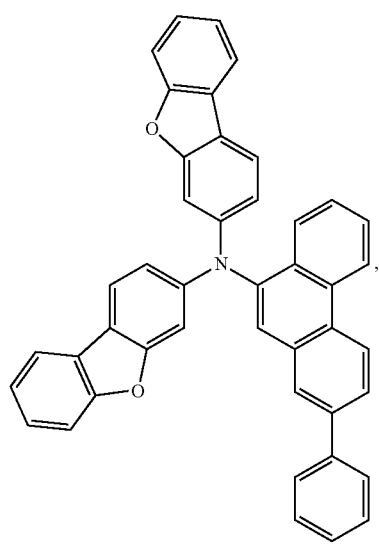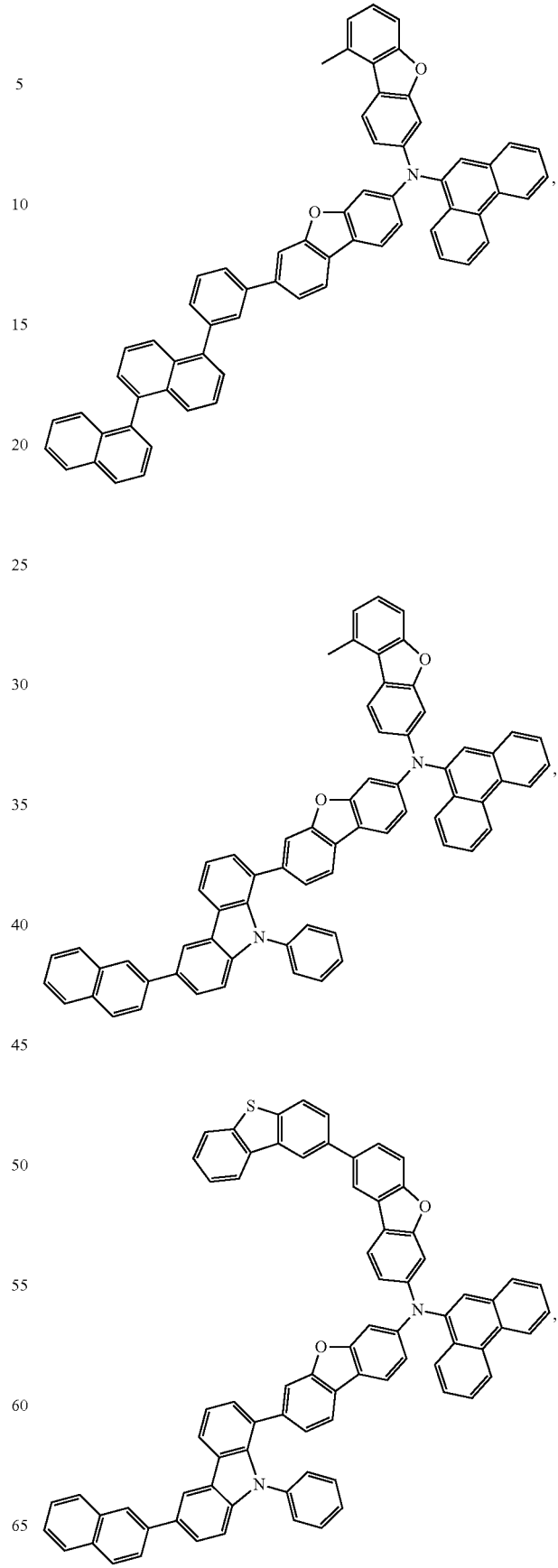

97
-continued
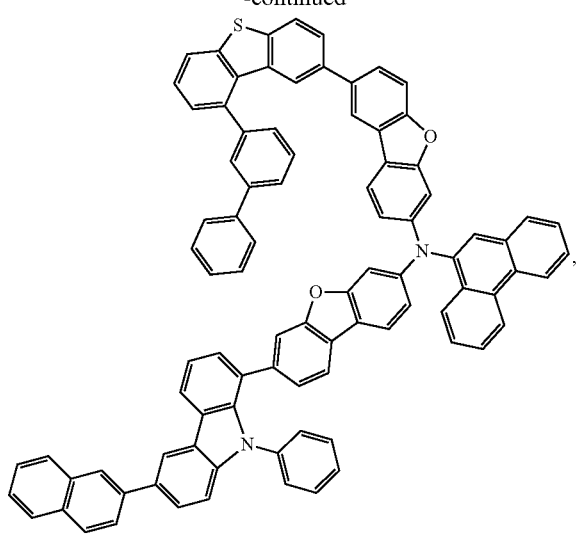
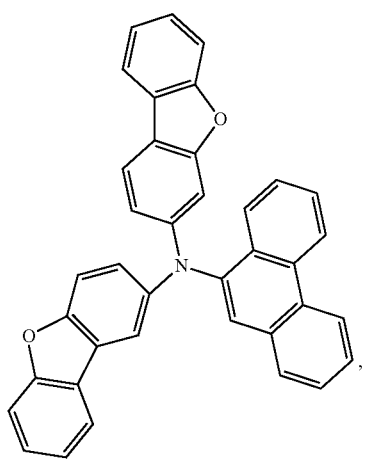
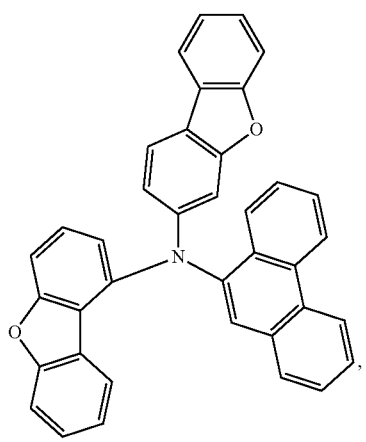
98
-continued
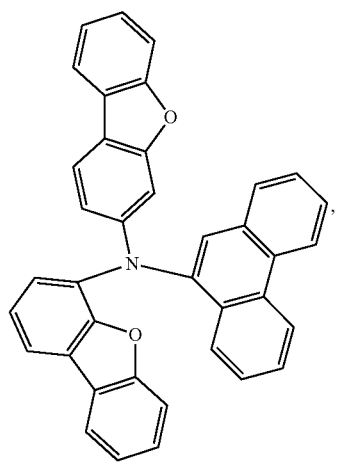
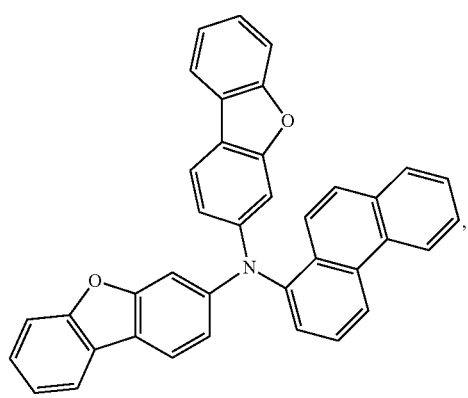
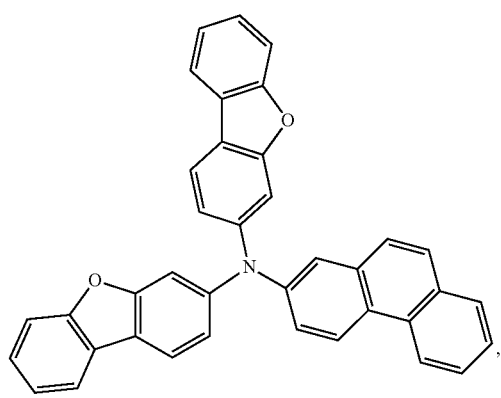

99
-continued
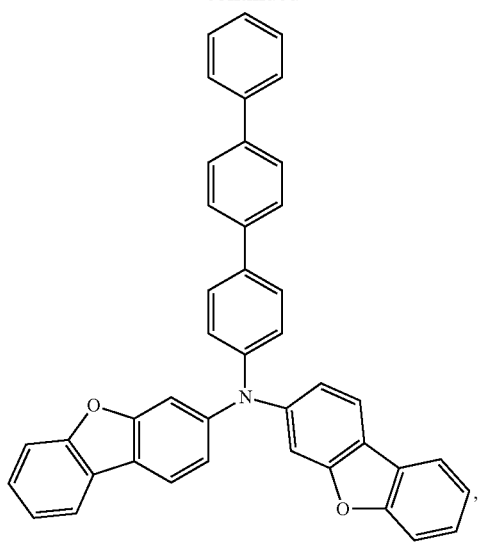
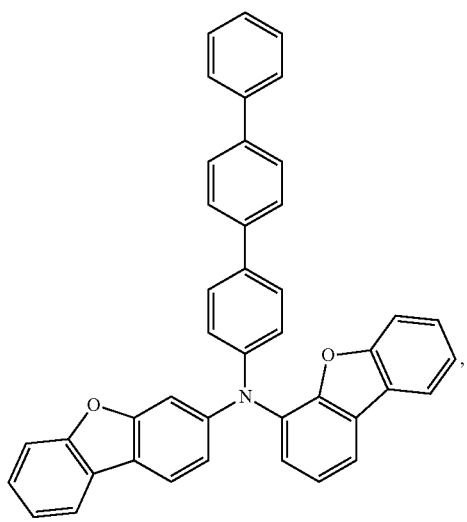
100
-continued
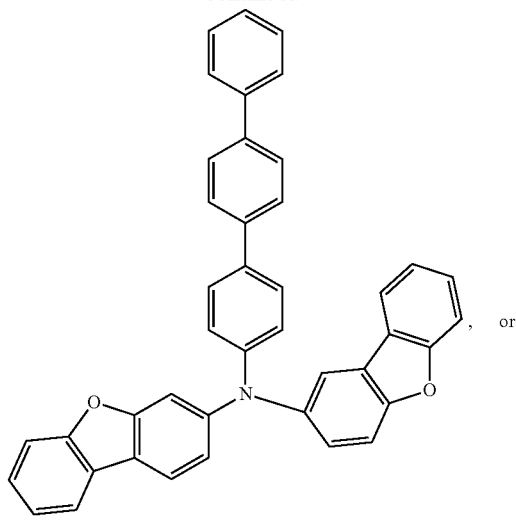, or
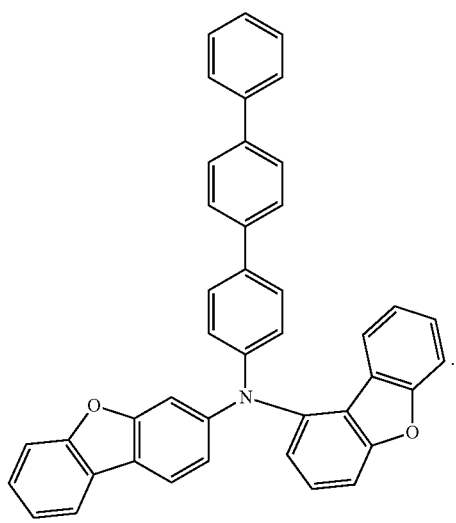.
* * * * *